(12) United States Patent
McDonald, III

(10) Patent No.: US 7,991,477 B2
(45) Date of Patent: Aug. 2, 2011

(54) METHODS FOR TREATING CENTRAL NERVOUS SYSTEM DAMAGE

(75) Inventor: John W. McDonald, III, Baltimore, MD (US)

(73) Assignee: Washington University, St. Louis, MO (US)

(*) Notice: Subject to any disclaimer, the term of this patent is extended or adjusted under 35 U.S.C. 154(b) by 141 days.

(21) Appl. No.: 12/557,634

(22) Filed: Sep. 11, 2009

(65) Prior Publication Data

US 2010/0114239 A1    May 6, 2010

Related U.S. Application Data

(63) Continuation of application No. 10/654,832, filed on Sep. 4, 2003, now Pat. No. 7,610,096.

(60) Provisional application No. 60/408,214, filed on Sep. 4, 2002.

(51) Int. Cl.
*A61N 1/18* (2006.01)

(52) U.S. Cl. .............................. 607/48; 607/50; 607/117

(58) Field of Classification Search ................... 607/48, 607/50, 117
See application file for complete search history.

(56) References Cited

U.S. PATENT DOCUMENTS

| | | | |
|---|---|---|---|
| 4,558,704 A | 12/1985 | Petrofsky | |
| 4,602,638 A | 7/1986 | Adams | |
| 4,719,922 A | 1/1988 | Padjen et al. | |
| 4,919,140 A | 4/1990 | Borgens et al. | |
| 5,002,053 A | 3/1991 | Garcia-Rill et al. | |
| 5,014,705 A | 5/1991 | Graupe et al. | |
| 5,121,747 A | 6/1992 | Andrews | |
| 5,269,303 A | 12/1993 | Wernicke et al. | |
| 5,634,462 A * | 6/1997 | Tyler et al. | 600/377 |
| 5,843,142 A | 12/1998 | Sultan | |
| 5,968,921 A | 10/1999 | Gold | |
| 5,974,342 A | 10/1999 | Petrofsky | |
| 6,163,725 A | 12/2000 | Peckham et al. | |
| 6,167,888 B1 | 1/2001 | Tuszynski et al. | |
| 6,210,974 B1 | 4/2001 | Gold | |
| 6,501,985 B1 | 12/2002 | Hirano et al. | |
| 6,988,004 B2 * | 1/2006 | Kanno et al. | 607/50 |
| 2004/0044381 A1 | 3/2004 | Duncan et al. | |
| 2004/0215290 A1 | 10/2004 | Zealear | |

FOREIGN PATENT DOCUMENTS

EP      0219204 A3     4/1987

(Continued)

OTHER PUBLICATIONS

Andrews et al., "Control of FES in paraplegia: modeling voluntary arm forces," Biomed. Mater. Eng., 1998, pp. 241-251, vol. 8.

(Continued)

*Primary Examiner* — Carl H Layno
*Assistant Examiner* — Natasha N Patel
(74) *Attorney, Agent, or Firm* — SNR Denton US LLP

(57) ABSTRACT

Methods for the treatment of CNS damage are described, and include inducing in a subject in need of such treatment, a therapeutically effective amount of functional electronic stimulation (FES) sufficient to evoke patterned movement in the subject's muscles, the control of which has been affected by the CNS damage. The induction of FES-evoked patterned movement at least partially restores lost motor and sensory function, and stimulates regeneration of neural progenitor cells in the subject patient.

27 Claims, 17 Drawing Sheets

FOREIGN PATENT DOCUMENTS

EP                0348535          3/1990

OTHER PUBLICATIONS

Andrews et al., "Hybrid FES orthosis incorporating closed loop control and sensory feedback," J. Biomed. Eng., 1988, pp. 189-195, vol. 10.

Ashworth, "Preliminary Trial of Carisoprodol in Multiple Sclerosis," The Practitioner, 1964, pp. 540-542.

Backman et al., "Case Studies, Single-Subject Research, and N of 1 Randomized Trials, Comparisons and Contrasts," Am. J. Phys. Med. Rehabil., 1999, pp. 170-176, vol. 78.

Bajd et al., "Restoration of walking in patients with incomplete spinal cord injuries by use of surface electrical stimulation—preliminary results," Prosthet. Orthot. Int., pp. 109-111, vol. 9.

Baker et al., "Chronic Blocade of Bioelectric Activity in Neonatal Rat Neocortex In Vitro: Physiolocal Effects," Int. J. Devl. Neuroscience, 1991, pp. 321-329, vol. 9.

Barbeau et al., "Recovery of Locomotion After Chronic Spinalization in the Adult Cat," Brain Research, 1987, pp. 84-95, vol. 412.

Barbeau et al., "Tapping into Spinal Circuits to Restore Motor Function," Brain Research Reviews, 1999, pp. 27-51, vol. 30.

Barres et al., "Proliferatino of Oligodendrocyte Precursor Cells Depends on Electrical Activity in Axons," Nature, 1993, pp. 258-260, vol. 361.

Becker et al., "Functional Electrical Stimulation Helps Replenish Neural Cells in the Adult CNS After Spinal Cord Injury," Washington University School of Medicine, pp. 1-25.

Behrman et al., "Locomotor Training After Human Spinal Cord Injury: A Series of Case Studies," Physical Therapy, 2000, pp. 688-700, vol. 80.

Benevento et al., "Gamma-Aminobutyric Acid and Somatostatin Immunoreactivity in the Visual Cortex of Normal and Dark-Reared Rats," Brain Research, 1995, pp. 172-182, vol. 689.

Blight, "Cellular Morphology of Chronic Spinal Cord Injury in the Cat: Analysis of Myelinated Axons by Line-Sampling," Neuroscience, 1983, pp. 521-543, vol. 10.

Bracken et al., "A Randomized, Controlled Trial of Methylprednisolone or Naloxone in the Treatment of Acute Spinal-Cord Injury," The New England J. Medicine, 1990, pp. 1405-1411, vol. 322.

Bracken et al., "Methylprednisolone or Tirilazad Mesylate Administration After Acute Spinal Cord Injury: 1-Year Follow Up," J. Neurosurg., 1998, pp. 699-706, vol. 89.

Brex et al., "Measurement of Spinal Cord Area in Clinically Isolated Syndromes Suggestive of Multiple Sclerosis," J. Neurol. Neurosurg. Psychiatry, 2001, pp. 544-547, vol. 70.

Bunge et al., "Observations on the Pathology of Human Spinal Cord Injury, A Review and Classification of 22 New Cases with Details from a Case of Chronic Cord Compression with Extensive Focal Demyelination," Advances in Neurology, 1993, pp. 75-89, vol. 59.

Carlson et al., "Acute Inflammatory Response in Spinal Cord Following Impact Injury," Experimental Neurology, 1998, pp. 77-88, vol. 151.

Chollet et al., "The Functional Anatomy of Motor Recovery After Stroke in Humans: A Study with Positron Emission Tomography," Ann. Neurol, 1991, pp. 63-71, vol. 29.

Cohen et al., "A Test of the 1992 International Standards for Neurological and Functional Classification of Spinal Cord Injury," Spinal Cord, 1998, pp. 554-560, vol. 36.

Coleman et al., "A Critical Appraisal of the Reporting of the National Acute Spinal Cord Injury Studies (II and III) of Methylprednisolone in Actue Spinal Cord Injury," J. Spinal Disorders, 2000, pp. 185-199, vol. 13.

Cooper-Kuhn et al., "Is It All DNA Repair? Methodological Considerations for Detecting Neurogenesis in the Adult Brain," Developmental Brain Res., 2002, pp. 13-21, vol. 134.

Corbetta et al., "Functional Reorganization and Stability of Somatosensory-Motor Cortical Topography in a Tetraplegic Subject with Late Recovery," PNAS, 2002, pp. 17066-17071, vol. 99.

Corner et al., "Spontaneous Firing as an Epigenetic Factor in Brain Development—Physiological Consequences of Chronic Tetrodotoxin Picrotoxin Exposure on Cultured Rat Neocortex Neurons," Developmental Brain Research, 1992, pp. 57-64, vol. 65.

Creasey et al., "An Implantable Neuroprosthesis for Restoring Bladder and Bowel Control to Patients with Spinal Cord Injuries: A Multicenter Trial," Arch. Phys. Med. Rehabil., 2001, pp. 1512-1519, vol. 82.

Cummings et al., "Bone Density at Various Sites for Prediction of Hip Fractures," The Lancet, 1993, pp. 72-75, vol. 341.

Dai et al., "Application of tilt sensors in functional electrical stimulation," IEEE Trans. Rehabil. Eng., 1996, pp. 63-72, vol. 4.

Dalby et al., "No Loss of Hippocampal Hilar Somatostatinergic Neurons After Repeated Electroconvulsive Shock: A Combined Stereological and In Situ Hybridization Study," Biol. Psychiatry, 1996, pp. 54-60, vol. 40.

Davies et al., "Adult Axon Regeneration in Adult CNS White Matter," Dept. of Neurosciences, Case Western Reserve University, 1 page.

Davis et al., "Paraplegia: prolonged closed-loop standing with implanted nucleus FES-22 stimulator and Andrews' foot-ankle orthosis," Stereotact. Funct. Neurosurg., 1997, pp. 281-287, vol. 69.

Davis et al., "Paraplegia: prolonged standing using closed-loop functional electrical stimulation and Andrews ankle-foot orthosis," Artif. Organs, 1999, pp. 418-420, vol. 23.

Davoodi et al., "Computer simulation of FES standing up in paraplegia: a self-adaptive fuzzy controller with reinforcement learning," IEEE Trans. Rehabil. Eng., 1998, pp. 151-161, vol. 6.

Davoodi et al., "Optimal control of FES-assisted standing up in paraplegia using genetic algorithms," Med. Eng. Phys., 1999, pp. 609-617, vol. 21.

Davoodi et al., "Predicting the voluntary arm forces in FES-assisted standing up using neural networks," Biol. Cybern., 2001, pp. 122-143, vol. 85.

Dean et al., "Cell-Cycle Analysis Using a Monoclonal Antibody to BrdUrd," Cell Tissue Kinet., 1984, pp. 427-436, vol. 17.

Demerens et all, "Induction of Myelination in the Central Nervous System by Electrical Activity," Proc. Natl. Acad. Sci. USA, 1996, pp. 9887-9892, vol. 93.

Dietz, "Spinal Cord Lesion: Effects of an Perspectives for Treatment," Neural Plasticity, 2001, pp. 83-90, vol. 8.

Dimitrijevic et al., "Motor Control in Man After Partial or Complete Spinal Cord Injury," Motor Control Mechanisms in Health and Disease, 1983, pp. 915-926.

Dimitrijevic, "Residual Motor Functions in Spinal Cord Injury," Advances in Neurology, 1988, pp. 139-155, vol. 47.

Dolan et al., "Switching curve controller for FES-assisted standing up and sitting down," IEEE Trans. Rehabil. Eng., 1998, pp. 167-171, vol. 6.

Dolbeare et al., "Bromodeoxyuridine: A Diagnostic Tool in Biology and Medicine, Part III. Proliferation in Normal, Injured and Diseased Tissue, Growth Factors, Differentiation, DNA Replication Sites and In Situ Hybridization," Histochemical J., 1996, pp. 531-575, vol. 28.

Donaldson et al., "FES Cycling May Promote Recovery of Leg Function After Incomplete Spinal Cord Injury," Spinal Cord, 2000, pp. 680-682, vol. 38.

Edgerton et al., "Retraining the Injured Spinal Cord," J. Physiology, 2001, pp. 15-22, vol. 533.

Elbert et al., "Extensive Reorganization of the Somatosensory Cortex in Adult Humans After Nervous System Injury," NeuroReport, 1994, pp. 2593-2597, vol. 5.

Field-Fote, "Combined Use of Body Weight Support, Functional Electric Stimulation, and Treadmill Training to Improve Walking Ability in Individuals with Chronic Incomplete Spinal Cord Injury," Arch. Phys. Med. Rehabil., 2001, pp. 818-824, vol. 82.

Furshpan, "Seizure-Like Activity in Cell Culture," Epilepsy Res., 1991, pp. 24-32, vol. 10.

Gage et al., "Survival and Differentiation of Adult Neuronal Progenitor Cells Transplanted to the Adult Brain," Proc. Natl. Acad. Sci. USA, 1995, pp. 11879-11883, vol. 92.

Gage, "Discussion Point, Stem Cells of the Central Nervous System," Current Opinion in Neurobiol., 1998, pp. 671-676, vol. 8.

Geinisman et al., "Unbiased Stereological Estimation of the Total Number of Synapses in a Brain Region," J. Neurocytology, 1996, pp. 805-819, vol. 25.
Geisler et al., "The Sygen® Multicenter Acute Spinal Cord Injury Study," Spine, 2001, pp. S87-S98, vol. 26.
Gledhill et al., "Demyelination and Remyelination After Acute Spinal Cord Compression," Experimental Neurology, 1973, pp. 472-487, vol. 38.
Gorman et al., "The Effect of Stimulus Parameters on the Recruitment Characteristics of Direct Nerve Stimulation," IEEE Transactions on Biomedical Engineering, 1983, pp. 407-414, vol. BME-30.
Granat et al, "The use of functional electrical stimulation to assist gait in patients with incomplete spinal cord injury," Disabil. Rehabil., 1992, pp. 93-97, vol. 14.
Granat et al., "Improving limb flexion in FES gait using the flexion withdrawal response for the spinal cord injured person," J. Biomed. Eng., 1993, pp. 51-56., vol. 15.
Granat et al., "The role of functional electrical stimulation in the rehabilitation of patients with incomplete spinal cord injury—observed benefits during gait studies," Paraplegia, 1993, pp. 207-215, vol. 31.
Griffiths et al., "Nerve Fibres in Spinal Cord Impact Injuries," J. Neurological Sciences, 1983, pp. 335-349, vol. 58.
Grill et al., "At the Interface: Convergence of Neural Regeneration and Neural Prostheses for Restoration of Function," J. Rehabilitation Research and Development, pp. 633-639, vol. 38.
Grill, Jr. et al., "The Effect of Stimulus Pulse Duration on Selectivity of Neural Stimulation," IEEE Transactions on Biomedical Engineering, 1996, pp. 161-166, vol. 43.
Guyatt et al., "Determining Optimal Therapy—Randomized Trials in Individual Patients," N. Engl. J. Med., 1986, pp. 889-892, vol. 314.
Hall et al., "Follow-Up Study on Individuals with High Tetraplegia (C1-C4) 14 to 24 Years Postinjury," Arch. Phys. Med. Rehabil., 1999, pp. 1507-1513, vol. 80.
Heller et al., "Swing-through gait with free-knees produced by surface functional electrical stimulation," Paraplegia, 1996, pp. 8-15, vol. 34.
Hendry et al., "Activity-Dependent Regulation of GABA Expression in the Visual Cortex of Adult Monkeys," Neuron, 1988, pp. 701-712, vol. 1.
Hendry et al., "Reduction in Number of Immunostained GABAergic Neurones in Deprived-Eye Dominance Columns of Monkey Area 17," Nature, 1986, pp. 750-753, vol. 320.
Horner et al., "Proliferation and Differentiation of Progenitor Cells Throughout the Intact Adult Rat Spinal Cord," J. Neuroscience, 2000, pp. 2218-2228, vol. 20.
Horner et al., "Regenerating the Damaged Central Nervous System," Nature, 2000, pp. 963-970, vol. 407.
Hurlbert, "The Role of Steroids in Acute Spinal Cord Injury," Spine, 2001, pp. S39-S46, vol. 26.
Ishii et al., "Increase of Oligodendrocyte Progenitor Cells After Spinal Cord Injury," J. Neuroscience Res., 2001, pp. 500-507, vol. 65.
Jenkins et al., "Reorganization of Neocortical Representations After Brain Injury: A Neurophysiological Model of the Bases of Recovery from Stroke," Progress in Brain Research, 1987, pp. 249-266, vol. 71.
Jones et al., "Intensive Exercise May Preserve Bone Mass of the Upper Limbs in Spinal Cord Injured Males but Does Not Retard Demineralisation of the Lower Body," Spinal Cord, 2002, pp. 230-235, vol. 40.
Kakulas et al., "White Matter Changes in Human Spinal Cord Injury," Chapter 15 of Spinal Cord Monitoring, 1998, pp. 395-407.
Kakulas, "A Review of the Neuropathology of Human Spinal Cord Injury with Emphasis on Special Features," Spinal Cord Med., 1999, pp. 119-124, vol. 22.
Kakulas, "The Applied Neuropathology of Human Spinal Cord Injury," Spinal Cord, 1999, pp. 79-88, vol. 37.
Kempermann et al., "New Nerve Cells for the Adult Brain," Scientific American, 1999, pp. 48-53.
Kirkwood et al., "Automatic detection of gait events: a case study using inductive learning techniques," J. Biomed. Eng., 1989, pp. 511-516, vol. 11.
Kirshblum et al., "Predicting Neurologic Recovery in Traumatic Cervical Spinal Cord Injury," Arch. Phys. Med. Rehabil., 1998, pp. 1456-1466 , vol. 79.
Kirtley et al., "Control of functional electrical stimulation with extended physiological proprioception," J. Biomed. Eng., 1990, pp. 183-188, vol. 12.
Kostov et al., "Machine learning in control of functional electrical stimulation systems for locomotion," IEEE Trans. Biomed. Eng., 1995, pp. 541-551, vol. 42.
Kuhn et al., "Neurogenesis in the Dentate Gyrus of the Adult Rat: Age-Related Decrease of Neuronal Progenitor Proliferation," J. Neuroscience, 1996, pp. 2027-2033, vol. 16.
Lin et al., "Re-expression of the Intermediate Filament Nestin in Reactive Astrocytes," Neurobiology of Disease, 1995, pp. 79-85, vol. 2.
Losseff et al., "T1 Hypointensity of the Spinal Cord in Multiple Sclerosis," J. Neurol., 2001, pp. 517-521, vol. 248.
Lovely et al., "Effects of Training on the Recovery of Full-Weight-Bearing Stepping in the Adult Spinal Cat," Experimental Neurology, 1986, pp. 421-435, vol. 92.
Magavi et al., "Identification of Newborn Cells by BrdU Labeling and Immunocytochemistry In Vivo," Methods in Mol. Biol., 2002, pp. 283-, vol. 198.
Maynard et al., "Neurological Prognosis After Traumatic Quadriplegia," J. Neurosurg., 1979, pp. 611-616, vol. 50.
Maynard, Jr. et al., "International Standards for Neurological and Functional Classification of Spinal Cord Injury," Spinal Cord, 1997, pp. 266-274, vol. 35.
McDonald et al., "Late Recovery Following Spinal Cord Injury," J. Neurosurg. (Spine 2), 2002, pp. 252-265, vol. 97.
McDonald et al., "Spinal-Cord Injury," Lancet, 2002, pp. 417-425, vol. 359.
McDonald et al., "Transplanted Embryonic Stem Cells Survive, Differentiate and Promote Recovery in Injured Rat Spinal Cord," Nature Medicine, 1999, pp. 1410-1412, vol. 5.
McDonald, "Repairing the Damaged Spinal Cord," Scientific American, 1999, pp. 65-73.
McTigue et al., "Proliferation of NG2-Positive Cells and Altered Oligodendrocyte Numbers in the Contused Rat Spinal Cord," J. Neurosci., 2001, pp. 3392-3400, vol. 21.
McTigue et al., "Strategies for Spinal Cord Injury Repair," Progress in Brain Res., 2000, pp. 3-8, vol. 128.
McTugue et al., "Neurotrophin-3 and Brain-Derived Neurotrophic Factor Induce Oligodendrocyte Proliferation and Myelination of Regenerating Axons in the Contused Adult Rat Spinal Cord," J. Neurosci., 1998, pp. 5354-5365, vol. 18.
Melton et al., "Long-Term Fracture Prediction by Bone Mineral Assessed at Different Skeletal Sites," J. Bone Mineral Res., 1993, pp. 1227-1233, vol. 8.
Micheva et al., "Neonatal Sensory Deprivation Induces Selective Changes in the Quantitative Distribution of GABA-Immunoreactive Neurons in the Rat Barrel Field Cortex," J. Comp. Neurol., 1995, pp. 574-584, vol. 361.
Miltner et al., "Effects of Constraint-Induced Movement Therapy on Patients with Chronic Motor Deficits After Stroke: A Replication," Stroke, 1999, pp. 586-592, vol. 30.
Ming et al., "Electrical Activity Modulates Growth Cone Guidance for Diffusible Factors," Neuron, 2001, pp. 441-452, vol. 29.
Monaghan et al., "FEB Support of Mobility in Stroke and Incomplete Paraplegic Persons," from http://sens.el.utwent.nl/research/biomechfes/fes.shtml, 3 pages.
National Spinal Cord Injury Association Resource Center's website: http://www.makoa.org/nscia/fact09/html, "Factsheet #9: Functional Electrical Stimulation, Clinical Applications in Spinal Cord Injury," 2003, 2 pages.
Nesathurai, "Steroid and Spinal Cord Injury: Revisiting the NASCIS 2 and NASCIS 3 Trials," J. Trauma: Injury, Infection, and Critical Care, pp. 1088-1093, vol. 45.
Nicholls et al., "Regeneration of Immature Mammalian Spinal Cord After Injury," Trends Neurosci., 1996, pp. 229-234, vol. 19.
Page et al., "Stroke Patients' and Therapists' Opinions of Constraint-Induced Movement Therapy," Clinical Rehabilitation, 2002, pp. 55-60, vol. 16.

Piepmeier et al., "Late Neurological Changes Following Traumatic Spinal Cord Injury," J. Neurosurg., 1988, pp. 399-402, vol. 69.
Ramakers et al., "Development in the Absence of Spontaneous Bioelectric Activity Results in Increased Sterotyped Burst Firing in Cultures of Dissociated Cerebral Cortex," Exp. Brain. Res., 1990, pp. 157-166, vol. 79.
Rivero-Melian, "Organization of Hindlimb Nerve Projections to the Rat Spinal Cord: A Choleragenoid Horseradish Peroxidase Study," J. Comparative Neurology, 1996, pp. 651-663, vol. 364.
Ross et al, "Pre-Existing Fractures and Bone Mass Predict Vertebral Fracture Incidence in Women," Annals of Internal Medicine, 1991, pp. 919-923, vol. 114.
Ruijter et al., "Chronic Blocade of BioElectric Activity in Neonatal Rat Cortex Grown In Vitro: Morphological Effects," Int. J. Devl. Neurosci., 1991, pp. 331-3318, vol. 9.
Rutherford et al., "Brain-Derived Neurotrophic Factor Mediates the Activity-Dependent Regulation of Inhibition of Neocortical Cultures," J. Neuroscience, 1997, pp. 4527-4535, vol. 17.
Salmons et al., "Simple Optical Switch for Implantable Devices," Med. & Biol. Eng. & Comput., 1991, pp. 554-556, vol. 29.
Sampson et al., "Functional electrical stimulation effect on orthostatic hypotension after spinal cord injury," Arch. Phys. Med. Rehabil., 2000, pp. 139-143, vol. 81.
Schallert et al., "Recovery of Function After Brain Damage: Severe and Chronic Disruption by Diazepam," Brain Research, 1986, pp. 104-111, vol. 379.
Schmanke et al., "Amphetamine and Task-Specific Practice Augment Recovery of Vibrissae-Evoked Forelimb Placing After Unilaberal Sensorimotor Cortical Injury in the Rat," J. Neurotrauma, 1997, pp. 459-468, vol. 14.
Schwab et al., "Degeneration and Regeneration of Axons in the Lesioned Spinal Cord," Physiological Reviews, 1996, pp. 318-370, vol. 76.
Schwab, "Repairing the Injured Spinal Cord," Science, 2002, pp. 1029-103, vol. 295.
Seil et al., "Morphological Correlates of Altered Neuronal Activity in Organotypic Cerebellar Cultures Chronically Exposed to Anti-GABA Agents," Developmental Brain Research, 1994, pp. 123-132, vol. 77.
Seil et al., "Reduced Cortical Inhibitory Synaptogenesis in Organotypic Cerebellar Cultures Developing in the Absence of Neuronal Activity," J. Comparative Neurology, 1994, pp. 366-377, vol. 342.
Shihabuddin et al., "Adult Spinal Cord Stem Cells Generate Neurons After Transplantation in the Adult Dentate Gyms," J. Neurosci., 2000, pp. 8727-8735, vol. 20.
Simons et al., "Early Experience of Tactile Stimulation Influences Organization of Somatic Sensory Cortex," Nature, 1987, pp. 694-697, vol. 326.
Steeves et al., "Permissive and Restrictive Periods for Brainstem-Spinal Regeneration in the Chick," Progress in Brain Research, 1994, pp. 243-262, vol. 103.
Swett et al., "The Somatotopic Organization of Primary Afferent Terminals in the DSuperficial Laminae of the Dorsal Horn of the Rat Spinal Cord," J. Comparative Neurology, 1985, pp. 66-77, vol. 231.
Taub et al., "An Operant Approach to Rehabilitation Medicine: Overcoming Learned Nonuse by Shaping," J. Experimental Analysis of Behavior, 1994, pp. 281-293, vol. 61.
Taub et al., "Constraint-Induced Movement Therapy: A New Family of Techniques with Broad Application to Physical Rehabilitation—A Clinical Review," J. Rehabilitation Research and Development, 1999, pp. 237-251, vol. 36.
Van Der Lee et al., "Forced Use of the Upper Extremity in Chronic Stroke Patients," Stroke, 1999, pp. 2369-2375, vol. 30.
Van Griethuysen et al., "Biomechanics of functional electrical stimulation," Prosthet. Orthot. Int, 1982, pp. 152-156, vol. 6.
Van Praag et al., "Running Increases Cell Proliferation and Neurogenesis in the Adult Mouse Dentate Gyrus," Nature Neuroscience, 1999, pp. 266-270, vol. 2.
Waters et al., "Definition of Complete Spinal Cord Injury," Paraplegia, 1991, pp. 573-581, vol. 29.
Waters et al., "Functional and Neurological Recovery Following Acute SCI," J. Spinal Cord Medicine, 1998, pp. 195-199, vol. 21.
Waters et al., "Motor and Sensory Recovery Following Complete Tetraplegia," Arch. Phys. Med. Rehabil., 1993, pp. 242-247, vol. 74.
Weed et al., "Reinnervation of the allograft larynx in the rat laryngeal transplant model," Otolaryngol. Head Neck Surg., 1995, pp. 517-529, vol. 113.
Wernig et al., "Laufband (Treadmill) Therapy in Incomplete Paraplegia and Tetraplegia," J. Neurotrauma, 1999, pp. 719-726, vol. 16.
Wernig et al., "Laufband Locomotion with Body Weight Support Improved Walking in Persons with Severe Spinal Cord Injuries," Paraplegia, 1992, pp. 229-238, vol. 30.
Wernig et al., "Maintenance of Locomotor Abilities Following Laufband (Treadmill) Therapy in Para- and Tetraplegic Persons: Follow-Up Studies," Spinal Cord, 1998, pp. 744-749, vol. 36.
West et al., "Unbiased Stereological Estimation of the Total Number of Neurons in the Subdivisions of the Rat Hippocampus Using the Optical Fractionator," The Anatomical Record, 1991, pp. 482-497, vol. 231.
Widick et al., "Awake evoked electromyography recording from the chronically implanted rat," Laryngoscope, 1994, pp. 420-425, vol. 104.
Williamson et al., "Detecting absolute human knee angle and angular velocity using accelerometers and rate gyroscopes," Med. Biol. Eng. Comput., 2001, pp. 294-302, vol. 39.
Williamson et al., "Gait event detection for FES using accelerometers and supervised machine learning," IEEE Trans. Rehabil. Eng., 2000, pp. 312-319, vol. 8.
Williamson et al., "Sensor systems for lower limb functional electrical stimulation (FES) control," Med. Eng. Phys., 2000, pp. 313-325, vol. 22.
Wolf et al., "Forced Use of Hemiplegic Upper Extremities to Reverse the Effect of Learned Nonuse Among Chronic Stroke and Head-Injury Patients," Experimental Neurology, 1989, pp. 125-132, vol. 104.
Zealear et al., "Determination of the optimal conditions for laryngeal pacing with the Itrel II implantable stimulator," Otolaryngol. Head Neck Surg., 2001, pp. 193-192, vol. 125.
Zealear et al., "Electrical stimulation of a denervated muscle promotes selective reinnervation by native over foreign motoneurons," J. Nerophysiol., 2002, pp. 2195-2199, vol. 87.
Zealear et al., "Technical approach for reanimation of the chronically denervated larynx by means of functional electrical stimulation," Ann. Otol. Rhinol. Laryngol., 1994, pp. 705-712, vol. 103.
Zealear et al., "The effects of chronic stimulation on laryngeal muscle reinnervation," ORL J. Otorhinolaryngol. Relat. Spec., 2000, pp. 87-95, vol. 62.
International Search Report issued Jun. 22, 2004, in the related application PCT/US03/27819.

* cited by examiner

FIG. 6

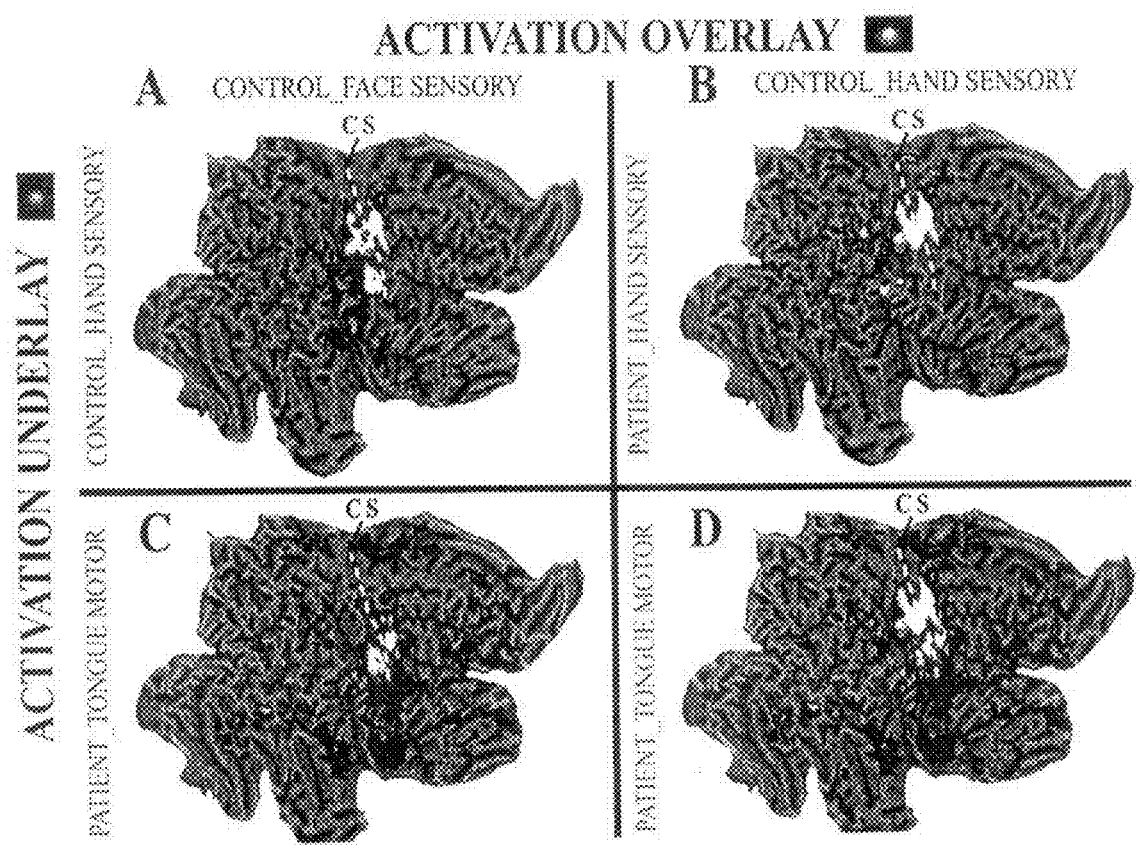

METHODS FOR TREATING CENTRAL NERVOUS SYSTEM DAMAGE

CROSS-REFERENCES TO RELATED APPLICATIONS

This application is a continuation application from U.S. application. Ser. No. 10/654,832 filed on Sep. 4, 2003, now U.S Pat. No. 7,610,096, which claims priority from Provisional Application Ser. No. 60/408,214 filed on Sep. 4, 2002, each of which is incorporated herein by reference in their entirety.

STATEMENT REGARDING FEDERALLY SPONSORED RESEARCH OR DEVELOPMENT

This invention was made in part with Government support under National Institutes of Health, National Institute of Neurological Disorders and Stroke Grant NS40520. The Government has certain rights in the invention.

BACKGROUND OF THE INVENTION

This invention relates in general to the field of medicine and to therapeutic methods for treating disruption of neural function resulting from damage to the central nervous system (CNS), and more particularly to methods for restoring motor and sensory function in subjects suffering from CNS damage.

Damage to the mammalian CNS can produce devastating physical impairment, and incur many added medical complications that in themselves can be life-threatening. CNS damage can result, for example, from spinal cord injury ("SCI"), which typically involves a complete or partial severance of a region of the spinal cord in an auto or other accident, or from a stroke-induced lesion. SCI can also be the result of a chronic disease process such as multiple sclerosis or a cancerous tumor. Acute trauma and chronic disease processes such as multiple sclerosis can also produce lesions elsewhere in the CNS that result in dramatic impairment of sensory or motor function, or both.

Besides impairment of motor and sensory function, additional medical consequences of CNS damage almost always arise. For example, medical complications resulting from substantial motor impairment include muscular atrophy, loss of bone mineral content, decubitus ulcers, urinary tract infections, muscle spasticity, impaired circulation, and reduced heart and lung capacity.

The American Spinal Injury Association ("ASIA") has developed international standards for examining and reporting the severity of spinal cord injury ("SCI"). Table 1 presents ASIA's five grades of spinal cord function, A to E, where E is normal. The ASIA Grade A describes individuals with the least remaining function. Such patients have little hope for recovery. Less than 1% of those with no muscle activity in the lower extremities 1 month after injury learn to walk again, and only 10% recover enough function to be reclassified as ASIA B or better. Approximately 90% of patients remain classified as ASIA Grade A.

TABLE 1

| Grade | Description |
|---|---|
| | ASIA's international standards for classifying SCI |
| A | Complete. No sensory or motor function preserved in sacral segments S4-S5 |
| B | Incomplete. Sensory but not motor function preserved below the neurologic level and extending through sacral segments S4-S5 |
| C | Incomplete. Motor function preserved below the neurologic level; majority of key muscle have a grade <3 |
| D | Incomplete. Motor function preserved below the neurologic level; majority of key muscles have a grade >3 |
| E | Normal motor and sensory function |

Patients with SCI are often told that improvement or recovery occurs largely in the first 6 months after injury and is complete by 2 years. Indeed, the literature does not provide a single example of an individual with an ASIA Grade A SCI who recovered by more than one grade 2 years after injury. Some delayed recoveries occur, but the timeframe is typically between 1 and 6 months after injury for large improvements. Such recoveries are most common when an accompanying head injury impedes initial progress. Small improvements can occur after periods longer than 2 years but typically occur in individuals with incomplete injuries.

Some number of individuals with ASIA Grade A SCI might have at least some functional connections across the SCI lesion. Indeed, it is rare for the cord to be completely severed by spinal trauma unless a gunshot or knife attack causes the wound. Studies performed in the 1950s indicate that limited preservation of white matter across the SCI lesion can sustain substantial spinal cord function. Preservation of less than 10% of the normal axon complement in the cat spinal cord can support walking, although this should not be viewed as the optimal requirement. Moreover, detailed anatomical post-mortem studies of chronic SCI in humans reveal that small residual connections across the lesion can preserve some function. For example, one individual with ASIA Grade C SCI had retained only 1.17 mm$^2$ of white matter at the level of the lesion. Another patient with some preserved motor function below the level of a cervical injury had only 3175 corticospinal axons—less than 8% of the number (41,472) found in normal controls.

A decade ago, the adult central nervous system ("CNS") was thought to be incapable of regeneration. Rehabilitation focused primarily on the immediate post-injury phase, when patients were still in the hospital, and aimed to maximize existing function and minimize complications. Although these goals are still important, the concept of spontaneous regeneration has emerged.

Current treatments for SCI are both limited and controversial. Administration of methylprednisolone within 8 hours of traumatic injury was one of the first drug therapies to receive support. Limitations in technical design and the marginal clinical effect of methylprednisolone seen in the original multicenter studies have raised concern about this approach. Other medications, including Naloxone and Tirilazad, have also been examined; however, those studied did not achieve their primary endpoints. Most recently, the ganglioside, GM-1, has shown promise when administered in the subacute injury period, although primary endpoints were again not achieved. In general, most rehabilitation approaches are accepted in the field but specific aspects have not been tested for efficacy in the SCI population. Moreover, the duration of inpatient rehabilitation has dramatically decreased over the last 10 years, necessitating the development of cost-effective in-home therapies.

Functional electrical Stimulation ("FES") has been used to restore certain functions following neural injury or disease. Examples include cochlear implants for restoration of hearing, stimulation of lower motor neurons to restore motor function including hand grasp and release, standing and stepping, breathing, and bladder emptying, and deep brain stimulation to treat the motor symptoms of Parkinson's disease (Grill and Kirsch, 1999; McDonald and Sadowsky, 2002). Each of these applications works by stimulating neural activity in existing neurons and muscles to restore control to systems where control has been compromised by injury or disease. However, FES has not been applied to reversing or altering disease progression or to promoting tissue regeneration or repair.

Locomotor training, such as on a treadmill, has been applied to motor incomplete patients (i.e., ASIA grade B or better) to enhance recovery of walking. Locomotor training can help such patients improve their walking speed and posture, and to relearn and maintain balance while walking. These improvements correlate well with corresponding improvements in muscle strength and in cardiovascular fitness, and are also believed to involve improved recruitment of existing, spared motor neurons. Locomotor therapy has been combined with partial body weight support (BWS) of up to 40%, to reduce the load borne by lower limbs during training, straighten walking posture, and assist certain aspects of gait such as swing and balance. BWS of greater than about 30-40% is generally thought to substantially limit any benefit of locomotor training to the patient.

FES therapy has been used in combination with locomotor or cycling training for motor incomplete patients. Field-Fote describes the combined use of FES with partial BWS and treadmill training, to improve over-ground walking ability in patients of ASIA grade C (Edelle C. Field-Fote, Arch. Phys. Med. Rehabil. 82: 818-24, (June 2001)). Patients were able to support at least 70% of their own body weight and were able to walk on a treadmill. Patients treated accordingly showed improved over-ground walking speed in the absence of BWS and FES, due to training effects on the musculoskeletal and cardiovascular systems. FES cycling has been described, for promoting recovery of leg strength and endurance in a motor incomplete patient (N. Donaldson et al., Spinal Cord 38:680-82 (2000)). FES cycling in the single subject resulted in increased leg muscle thickness and voluntary leg strength. However, only motor incomplete patients have been deemed to derive a benefit from FES therapy, or from locomotor training, or from a combination of the two, because the benefits of such therapy are linked to the training effects on existing, spared (i.e. undamaged) elements of the patient's neuromuscular system. Accordingly, since such training effects are obviated by the extreme injury and lack of sparing in motor complete patients, FES therapy and locomotor therapy have not even been tried with such patients.

A great need therefore remains for novel approaches to partially or completely restoring lost or impaired sensory and motor function in individuals suffering from disruptions of motor and sensory function due to damage of the CNS.

BRIEF SUMMARY OF THE INVENTION

The present invention provides a novel approach to restoring motor and sensory function in individuals suffering from CNS damage including those individuals with such extensive CNS damage that recovery of any function requiring the activity of the lost or damaged neurons was previously thought impossible. The methods are based in part on surprising findings in a motor complete human subject with a high cervical (C2) traumatic injury. The patient showed only spotty sensation in the left hemibody over the five years following the injury. When treated with a regimen of physical therapy that included application of functional electrical stimulation (FES) sufficient to evoke patterned movement in the subject's lower limbs, the subject showed unexpected, late partial recovery of motor function during years 6-8 post-injury. The methods are also based in part on complementary experimental findings in a rat model of spinal cord injury, which demonstrate the surprising effects of the current methods on neural cell regeneration and on motor function in rat.

Accordingly, a method for treating central nervous system (CNS) damage in a mammalian subject in need of such treatment includes exposing the mammalian subject to a therapeutically effective amount of functional electrical stimulation (FES)-evoked patterned movement. According to an exemplary embodiment, exposing the mammalian subject to a therapeutically effective amount of FES-evoked patterned movement includes exposure for a period of time sufficient to regenerate neural cells in the CNS of the subject.

In another embodiment, the methods encompass a method for regenerating neural cells in a subject suffering from CNS damage includes applying functional electronic stimulation (FES) to muscles of the subject that are in communication with peripheral nervous system nerves of the subject, the FES being sufficient to evoke patterned movement of limbs of the subject, so that the patterned movement in conjunction with the FES regenerates neural cells in the subject by promoting neural cell birth and survival in the CNS of the subject.

In another embodiment, the methods encompass a method for repairing CNS damage in a subject in need of such treatment includes regenerating neural cells in or around a site of the CNS damage using functional electronic stimulation-evoked patterned movement.

In another embodiment, the methods encompass a method for at least partially restoring sensory or motor function in a subject suffering from CNS damage, the method including inducing in the subject an amount of FES-evoked patterned movement sufficient to at least partially restore motor or sensory function previously unattainable for the patient due to the CNS damage.

In another embodiment, the methods encompass a method for at least partially restoring motor function in a motor complete subject including inducing in the subject a therapeutically effective amount of FES-evoked patterned movement.

In another embodiment, the methods encompass a method for at least partially restoring sensory function in a sensory complete subject including inducing in the subject a therapeutically effective amount of FES-evoked patterned movement.

In another embodiment, the methods encompass a method for at least partially restoring motor and sensory function in a subject who is both motor and sensory complete, including inducing in the subject a therapeutically effective amount of FES-evoked patterned movement.

In another embodiment, the methods encompass a method for treating spinal cord injury including identifying a motor complete or sensory complete subject in need of such treatment, regenerating neural cells in the spinal cord of the subject using functional electronic stimulation-evoked patterned movement, and monitoring of the subject during and after the course of said treatment to assess the effectiveness of the neural cell regeneration.

In another embodiment, the methods encompass a method for late recovery of sensory or motor function in a subject suffering from CNS damage, including inducing in the subject a therapeutically effective amount of FES-evoked patterned movement to muscles the control of which has been affected by the CNS damage wherein the induction of FES-evoked patterned movement is begun more than six months after the CNS damage occurs.

In another embodiment, the methods encompass a method for regenerating neural cells in a subject suffering from CNS damage that includes applying functional electronic stimulation (FES) to muscles of the subject that are in communication with peripheral nervous system nerves of the subject, the FES being sufficient to stimulate a central pattern generator coordinating patterned movement of limbs of the subject, so that the stimulation of the central pattern generator regenerates neural cells in the subject by promoting neural cell birth and survival in the CNS of the subject.

In another embodiment, the methods encompass a method for repairing CNS damage in a subject in need of such treatment includes regenerating neural cells in or around a site of the CNS damage FES stimulation of a central pattern generator.

In another embodiment, the methods encompass a method for at least partially restoring sensory or motor function in a subject suffering from CNS damage, the method including stimulating a central pattern generator in the subject using FES configured to evoke a patterned movement in the subject.

These and other features, aspects and advantages of the present invention will become better understood with reference to the following description, examples and appended claims.

BRIEF DESCRIPTION OF THE DRAWINGS

FIG. 6 is a schematic drawing comparing the human patient's ASIA grades from 1995 to 2002;

FIG. 17 is a comparison of functional topography in primary somatosensory cortex (SI), between the human subject with SCI and control subjects.

DETAILED DESCRIPTION OF THE INVENTION

Definitions

Figure 1:
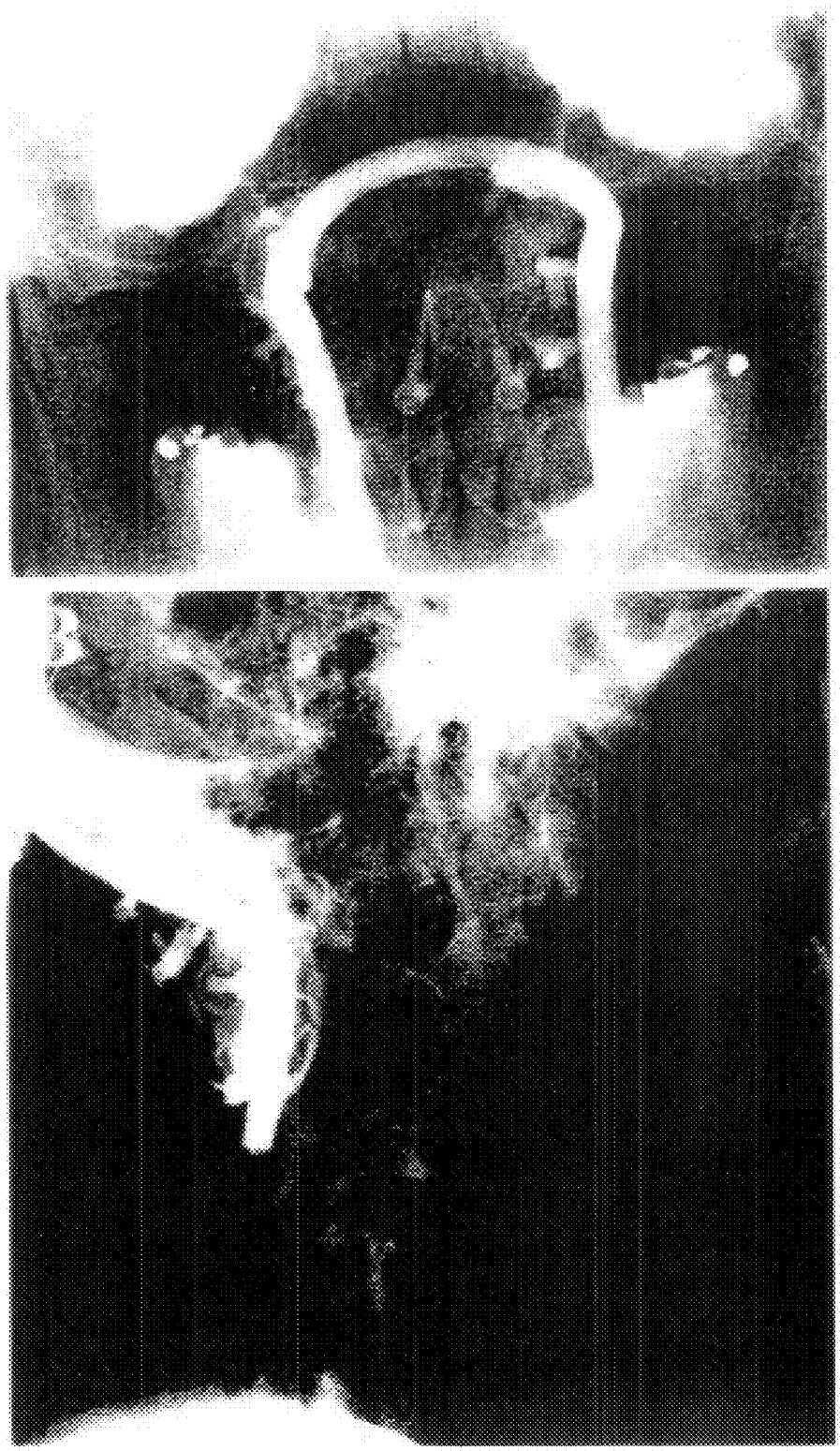
FIG. 1 shows x-ray films revealing an open mouth view (A) and a lateral view (B) of the cervical spine following internal stabilization in a human subject with SCI.

To facilitate understanding of the invention, certain terms as used herein are defined below as follows:

As used herein, the term "therapeutically effective" refers to a characteristic of an amount of FES-evoked patterned movement, wherein the amount is sufficient to at least partially restore previously lost motor or sensory function or previously lost motor and sensory function, together with regeneration of neural cells in the subject. In subjects such as motor complete or sensory complete subjects, regeneration of neural cells is deemed to occur when at least partial restoration of previously lost function is observed. In other subjects where the existence of undamaged, spared neurons may partially contribute to recovery of function, regeneration of neural cells can be evaluated using fMRI and other imaging techniques, or other methods of tissue evaluation as known in the art.

As used herein, the terms "regenerate" and "regeneration" refer to the enhanced birth and survival of neuroepithelial-derived cells of the central nervous system, including particularly cells of the spinal cord, within or surrounding a site of cell damage. Neural regeneration shall be understood to at least partially restore or enhance neuronal signaling through or around the site of cell damage.

As used herein, the term "neural cells" encompasses tripotential progenitor cells, glial progenitor cells, astrocytes and oligodendrocytes, or any combination thereof, as well as any other cells that may derive developmentally from the neuroepithelium.

As used interchangeably herein, the terms "central nervous system damage" and "CNS damage" refer to the result of a disease process or injury that is characterized by destruction of, or harm to, cells of the brain or the spinal cord, such that the normal motor and sensory control function of the brain or spinal cord is disrupted. CNS damage shall be understood to encompass, for example, the result of an acute traumatic break or injury of the spine that completely or partially severs the spinal cord, the result of a stroke, the result of chronic disease such as multiple sclerosis, Huntington's Disease, Alzheimer's disease, amyotrophic lateral sclerosis (ALS) and neurodegeneration of aging, and the result of cancerous tumors forming within the central nervous system. A subject suffering from CNS damage is deemed to also be suffering from at least a partial disruption of motor or of sensory function, or of both motor and sensory function as a result of the CNS damage.

As used interchangeably herein, the terms "spinal cord injury" or "SCI" refer to a specific instance of CNS damage characterized by complete or partial destruction of the spinal cord at one or more sites, which may result from acute trauma to the spine or from a disease process.

As used interchangeably herein, the terms "functional electrical stimulation" and "FES" refer to a form of electrotherapy in which external electric current is applied to a muscle or muscle group to thereby evoke a bodily movement that normally would be subject to voluntary or involuntary control by the CNS.

As used interchangeably herein, the terms "central pattern generator" and "spinal pattern generator" refer to a group of nerve cells in the central nervous system, particularly in the spinal cord, that interact in a circuit to produce a coordinated pattern of signals that stimulate muscles to contract in sequence. An example is the alternating movements of leg muscles during walking. Although all the nerve cells in the central pattern generator may be located in the spinal cord, the activity of the circuit is normally modulated by signals from the brain, so that the activity is normally under voluntary control.

As used herein, the term "patterned movement" refers to motor activity of a subject, in which a body part or parts, typically a limb or limbs such as the legs, follow a coherent and repetitive or cyclical trajectory. When more than one body part is involved in a patterned movement, the body parts maintain a discernible coherent interrelationship during the motor activity. Examples of patterned movement include walking, breathing, biking, punching, kicking, swimming, fist clinching, toe pointing, knee bending, hip flexing, sitting, standing, and jumping.

As used herein, the term "FES-evoked" is used to described motor activity of a subject that is partially or completely elicited by administration of electrical stimulation to muscles of the body parts involved in the motor activity.

As used herein, the term "reciprocal movement" refers to a type of patterned movement in which at least two limbs, such as a pair of legs, move through at least two alternating positions in inverse relation to one another. Examples of reciprocal movement include the activity of two legs in walking or in biking motion.

As used herein, the term "neural signal" refers to an electrochemical depolarization or hyperpolarization, or a combination thereof, of a neural cell, that transmits information between neural cells. A neural signal may be an action potential, consisting of a stereotyped sequence of depolarization and repolarization of the cell membrane that transmits information through the cell from the input of the cell to its output. A neural signal alternatively be a local hyperpolarization or depolarization of the cell membrane that renders the cell either more or less likely to fire and action potential.

As used herein, the term "subject" refers to a mammal, including humans and nonhuman primates, dogs, cats, horses, cows, sheep, rabbits, mice, rats, and guinea pigs.

The present invention is based on the surprising discovery that a treatment regimen including induction of FES sufficient to evoke patterned movement in a subject suffering from CNS damage, such as a motor complete subject, at least partially restores previously lost CNS function and regenerates neural cells in or around a site of CNS damage. Accordingly, the present invention provides a novel approach to at least partially restoring motor and sensory function in individuals suffering from CNS damage, and particularly those individuals with such extensive CNS damage that recovery of any function requiring the activity of the lost or damaged neurons was previously thought impossible.

The methods are based in part on surprising findings in a human subject with a high cervical (C2) traumatic injury, clinically assessed as motor complete. The patient showed only spotty sensation in the left hemibody over the five years following the injury. When treated with a regimen of physical therapy that included application of functional electrical stimulation (FES) sufficient to evoke patterned movement in the subject's lower limbs, the subject showed unexpected, late partial recovery of motor function during years 6-8 post-injury. The methods are also based in part on complementary experimental findings in a rat model of spinal cord injury which, consistent with the human findings, demonstrate the surprising effects of the current methods on neural cell regeneration and on motor function in rat.

Conventional thinking has held that nerves in the adult mammalian CNS will not and cannot be induced to regenerate. Thus, recovery of lost CNS function in a patient suffering from CNS damage has previously been limited to that function that can be recovered solely through retraining existing, undamaged (i.e. "spared") neural cells. By "retraining" is meant application of a therapeutic regimen such as locomotor training that may result in improved function through recruitment of existing, undamaged motor neurons and from the induction of synaptic changes among existing neurons and between neuron and muscle fibers, such that the existing, undamaged cells are more efficiently used.

In contrast, Applicants have discovered that inducing FES-evoked patterned body movements regenerates neural cells such that CNS damage previously thought beyond repair is repaired, and function previously thought permanently lost is at least partially restored. Without being bound to a particular theory, the FES-evoked patterned movements are thought to stimulate neural regeneration by stimulating neural activity in a central pattern generator. Physiologic and metabolic demands placed on cells comprising the spinal circuit may activate cellular processes that promote new neural cell birth and survival.

Accordingly, the methods of the present invention encompass a method for treating CNS damage in a mammalian subject in need of such treatment, including inducing in the mammalian subject to a therapeutically effective amount of FES-evoked patterned movement. The therapeutically effective amount of FES-evoked patterned movement involves, in part, exposing the subject to the FES-evoked patterned movement for a period of time sufficient to regenerate neural cells, including the neural progenitor cells known as tripotential progenitor cells, as well as glial progenitors, astrocytes and oligodendrocytes. The regeneration is a result of enhanced neural cell birth or survival, or both enhanced birth and survival, as demonstrated by the anti-BrdU cell labeling results described infra. Further, as demonstrated by the human findings and corresponding rat data, FES-evoked patterned movement at least partially restores function by enhancing neural signal transmission capacity in or around a site of CNS damage, such as in or around a spinal cord lesion. The resultant at least partial restoration of function is also consistent with synaptic changes in both new and pre-existing neural cells form new synaptic connections among the cells in or around a site of CNS damage.

In an exemplary embodiment as described infra, the FES-evoked patterned movement is biking movement of the legs of a human subject, and the FES is applied to at least one leg muscle or muscle group. However, depending on the patterned movement selected for therapy, the muscle or muscle groups selected for induction of FES will be selected as appropriate from, for example, the gluteals, paraspinals, abdominals, wrist extensors, wrist flexors, deltoids, biceps, triceps, hamstrings, and quadriceps.

In general, the methods contemplate application of FES sufficient to evoke a patterned movement of limbs that results from a cycle of neural activity that is initiated in the peripheral nerves, propagates to the spinal cord, is followed by neural inactivity first in the peripheral nerves and then in the spinal cord, and then the cycle of neural activity is repeated. However, the actual elicitation of movement, particularly in a severely compromised patient such a motor complete patient several years post-injury, is not required to obtain neural regeneration. FES sufficient to stimulate a central pattern generator that coordinates the patterned movement, will produce the same effect. Thus, the methods also contemplate patterned electrical activation of a central pattern generator, regardless of whether movement is actually effected, to regenerate neural cells and at least partially restore function. This embodiment is especially suitable for treating severely compromised patients, such as the human subject of Example 1, whose muscle strength has been severely compromised by atrophy over months and years post-injury. Initially, partial restoration of function is obtained by regenerating neural cells using FES induced activation of a central pattern generator. Later, as improvement of function permits, continued and further improvements are obtained by the FES-induced activation of the central pattern generator which also effects actual movement.

Stimulation protocols are generally known in the arts of physical therapy and rehabilitation and are described for example in G. M. Yarkony et al., Arch. Phys. Med. Rehabil. 73:78-86 (1992). However, in an exemplary embodiment, a therapeutically effective amount of FES-evoked patterned movement is attained by inducing FES sufficient to evoke patterned movement for at least about one hour per day and at least three times per week. An example of an effective level of electronic stimulation within the meaning of the present invention is electronic stimulation delivered at 3 V, and using 200 µs monophasic pulses delivered at 20 Hz, as described in Examples 1 and 2. The FES may be induced through externally placed electrodes and connectors, i.e. on the skin, or through internally placed electrodes, such as implanted electrodes.

The effects of FES are assessed by clinical assessment of ASIA grade, and by the use of other clinical criteria and imaging techniques as known in the art that indicate regeneration of neural cells in or around the site of CNS damage. In a clinically complete patient, for example, partial recovery of function that corresponds to an improvement of at least one ASIA grade, with respect to motor or to sensory function, is indicative that regeneration has occurred. In patients assessed as clinically incomplete, the effects of FES are assessed using a combination of clinical criteria including improvement of at least one ASIA grade, time elapsed from the original injury, and as needed, imaging techniques such as fMRI that reveal neural regeneration. For example, FES is deemed to have regenerated neural cells in a patient clinically assessed as motor incomplete who has previously shown no significant improvement for about 6 months post-injury, but then shows substantial improvement of function corresponding to at least one ASIA grade after being exposed to FES in accordance with the methods described. FES is deemed to have regenerated neural cells in a motor incomplete patient or a sensory incomplete patient in whom the previously lost motor or sensory function is at least partially restored to a level corresponding to an improvement of at least one ASIA grade, and wherein the restored function was previously unattainable solely through retraining existing, undamaged (i.e. "spared") neural cells. The assessment of FES effects can be supplemented with the use of fMRI or other imaging techniques such as those relying on paramagnetic tracers to further reveal and characterize the neural regeneration.

In another embodiment, the methods encompass a method for regenerating neural cells in a subject suffering from CNS damage, the method including applying FES to muscles of the subject that are in communication with peripheral nervous system nerves of the subject, the FES being sufficient to evoke patterned movement of limbs of the subject, wherein the patterned movement in conjunction with the FES of the peripheral nervous system nerves regenerates neural cells in the subject by promoting neural cell birth and survival in the CNS of the subject. The methods encompass treating a subject who is either motor complete, or sensory complete, or both. The methods also encompass treating a subject who is motor incomplete or sensory incomplete or both wherein such a patient is characterized by CNS damage that cannot be recovered by retraining of existing, undamaged neurons.

The regeneration of neural cells and resulting at least partial restoration of motor function or sensory function or of both motor and sensory function involves restored transmission of a neural signal. In the case of a spinal cord lesion, for example, a partial restoration of function involves an at least partially restored neural signal that can cross the site of spinal cord injury. The at least partially restored neural signal can then be used by the subject to initiate voluntary control, including voluntary motor control for example, of a muscle previously denervated as a result of spinal cord lesion or as a result of other CNS damage.

In another embodiment, the methods contemplate a method for treating CNS damage in a subject in need of such treatment, the methods including regenerating neural cells in or around a site of CNS damage using functional electronic stimulation-evoked movement.

Alternatively, the methods encompasses at least partially restoring sensory or motor function in a subject suffering from CNS damage by inducing in the subject an amount of FES-evoked patterned movement sufficient to at least partially restore motor or sensory function previously unattainable for the patient due to the CNS damage. By "unattainable" is meant CNS function that cannot be recovered solely through retraining existing, undamaged (i.e. "spared") neural cells.

Another embodiment contemplates a method for treating spinal cord injury including identifying a motor complete or sensory complete subject in need of such treatment, regenerating neural cells in the spinal cord of the subject using functional electronic stimulation-evoked patterned movement, and monitoring the subject during and after the course of said treatment to assess the effectiveness of the neural cell regeneration.

EXAMPLES

Without further elaboration, it is believed that one skilled in the art can, using the preceding description, utilize the present invention to its fullest extent. The following specific examples are offered by way of illustration only and not by way of limiting the remaining disclosure.

Example 1

Neural Regeneration in Humans

Spinal cord injury (SCI) is a well-known cause of CNS damage resulting in substantial or total loss of CNS function, including loss of sensory or of motor function, or both depending on the precise nature of the injury. Use of the inventive therapy for late recovery from SCI injury may result in substantial if not complete restoration of motor and sensory function, even with a stable ASIA Grade A injury. Such partial restoration of function is possible even when the late recovery is well beyond the 6-months-from-injury time frame previously accepted as the period within which large improvements are possible for ASIA Grade A patients. According to the methods of the present invention, late recovery of function is possible even several years after injury.

This prospective, single-case study evaluated the potential for functional recovery from chronic spinal cord injury (SCI). The results are described fully in McDonald et al, *J. Neurosurg. (Spine 2)* 97:252-65 (2002), which is herein incorporated by reference in its entirety, together with the primary references contained therein. The patient was motor complete with minimal and transient sensory perception in the left hemibody. His condition was classified as C-2 American Spinal Injury Association (ASIA) Grade A and he had experienced no substantial recovery in the first 5 years after traumatic SCI. Clinical experience and evidence from the scientific literature suggest that further recovery would not take place. When the study began in 1999, the patient was tetraplegic and unable to breathe without assisted ventilation; his condition classification persisted as C-2 ASIA Grade A.

FIG. 1 shows x-ray films revealing an open mouth view (A) and a lateral view (B) of the cervical spine following internal stabilization. The type of injury incurred by this patient leads to bone dissociation of the head and spine. Reconstruction required fusion of the occiput to C-2 with titanium rods, wire, and bone graft.

Magnetic resonance imaging revealed severe injury at the C-2 level that had left a central fluid-filled cyst surrounded by a narrow donut-like rim of white matter. Five years after the injury a program known as "activity-based recovery" was instituted. The hypothesis was that patterned neural activity might stimulate the central nervous system to become more functional, as it does during development. Specifically, FES-evoked bicycling movement was induced in the subject, three times weekly, for about one hour per session.

Figure 2:
FIG. 2 shows schematic drawings of an FES bicycle.

FIG. 2 shows schematic drawings of the FES bicycle. The FES bicycle uses computer-controlled electrodes to stimulate the legs muscles in specific patterns. A paralyzed individual can therefore rotate the bicycle wheels even though he is unable to control his leg muscles voluntarily. In this study, three muscle groups (red) were stimulated bilaterally: the gluteal, quadriceps, and hamstring muscles. Electrodes (blue) went to pads attached to the skin over each muscle: two pads for each quadriceps (1) and one for each hamstring (2) and gluteal muscle (3).

Over a 3-year period (5-8 years after injury), the patient's condition improved from ASIA Grade A to ASIA Grade C, an improvement of two ASIA grades. Motor scores improved from 0/100 to 20/100, and sensory scores rose from 5-7/112 to 58-77/112. Using electromyography, the inventors documented voluntary control over important muscle groups, including the right hemidiaphragm (C3-5), extensor carpi radialis (C-6), and vastus medialis (L2-4). Reversal of osteoporosis and an increase in muscle mass was associated with this recovery. Moreover, spasticity decreased, the incidence of medical complications fell dramatically, and the incidence of infections and use of antibiotic medications was reduced by over 90%. These improvements occurred despite the fact that less than 25 $mm^2$ tissue (about 25%) of the outer cord (presumably white matter) had survived at the injury level.

History: This 42-year-old, right-handed man sustained a displaced C-2 Type II odontoid fracture due to an equestrian accident on May 27, 1995. The mechanism of injury was direct axial loading. The patient's horse stopped suddenly; the patient's hands were caught in the reins and his 6 ft 4 in, 230-lb body was projected over the horse's head. He landed directly on the helmet in a near-perpendicular position. He was rendered apneic but was maintained at the scene immediately with artificial respiration. He was transferred to the University of Virginia Hospital.

Figure 3:
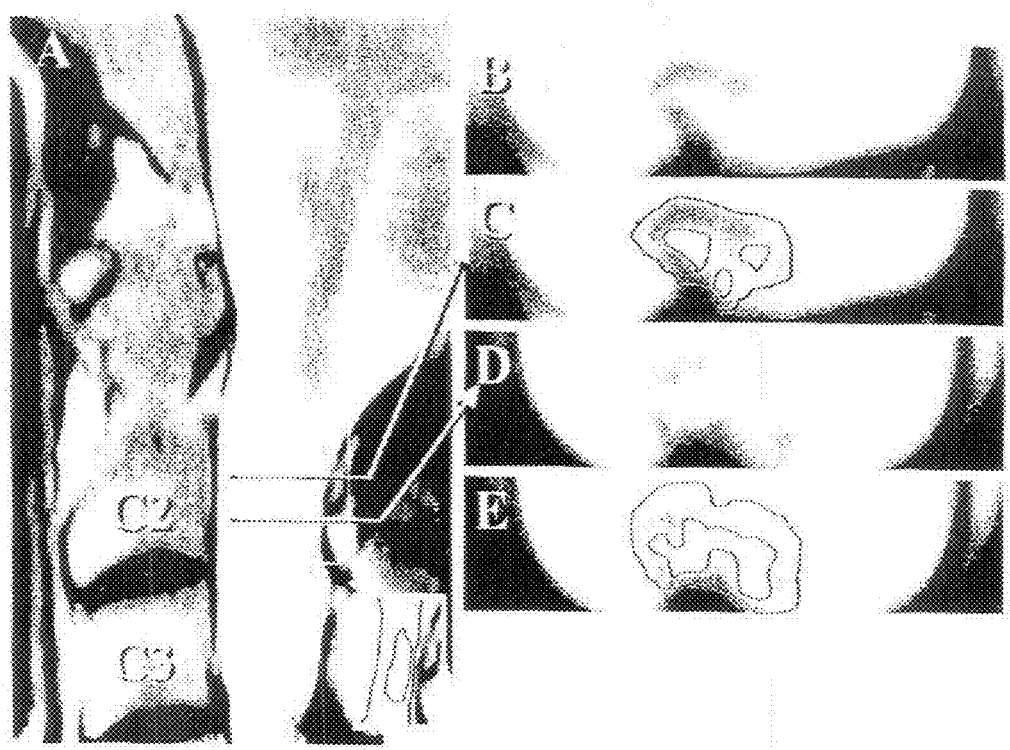
FIG. 3 shows serial MR images of the cervical spinal cord demonstrating a posttraumatic cyst at C-2 level and severe encephalomalacia in the subject, a human patient who suffered a traumatic SCI 5 years earlier.
Figure 3:
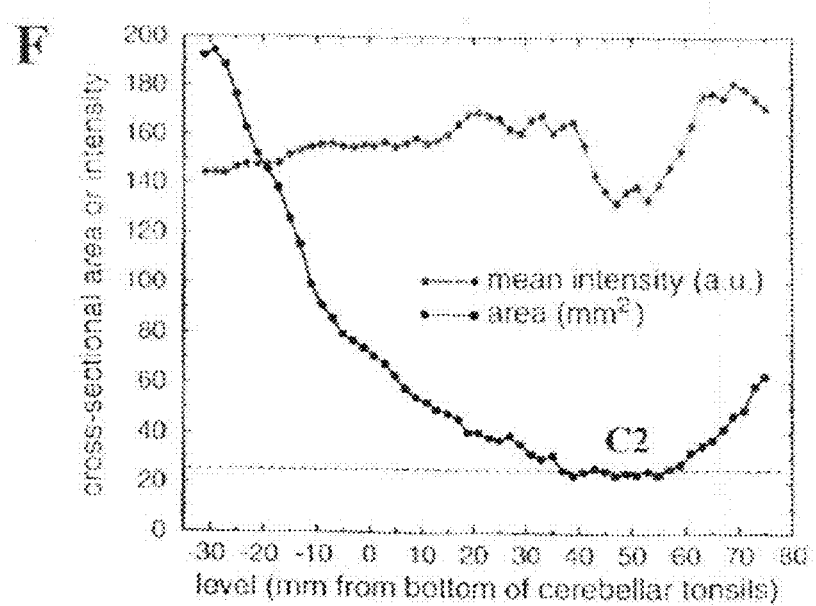
Figure 4:
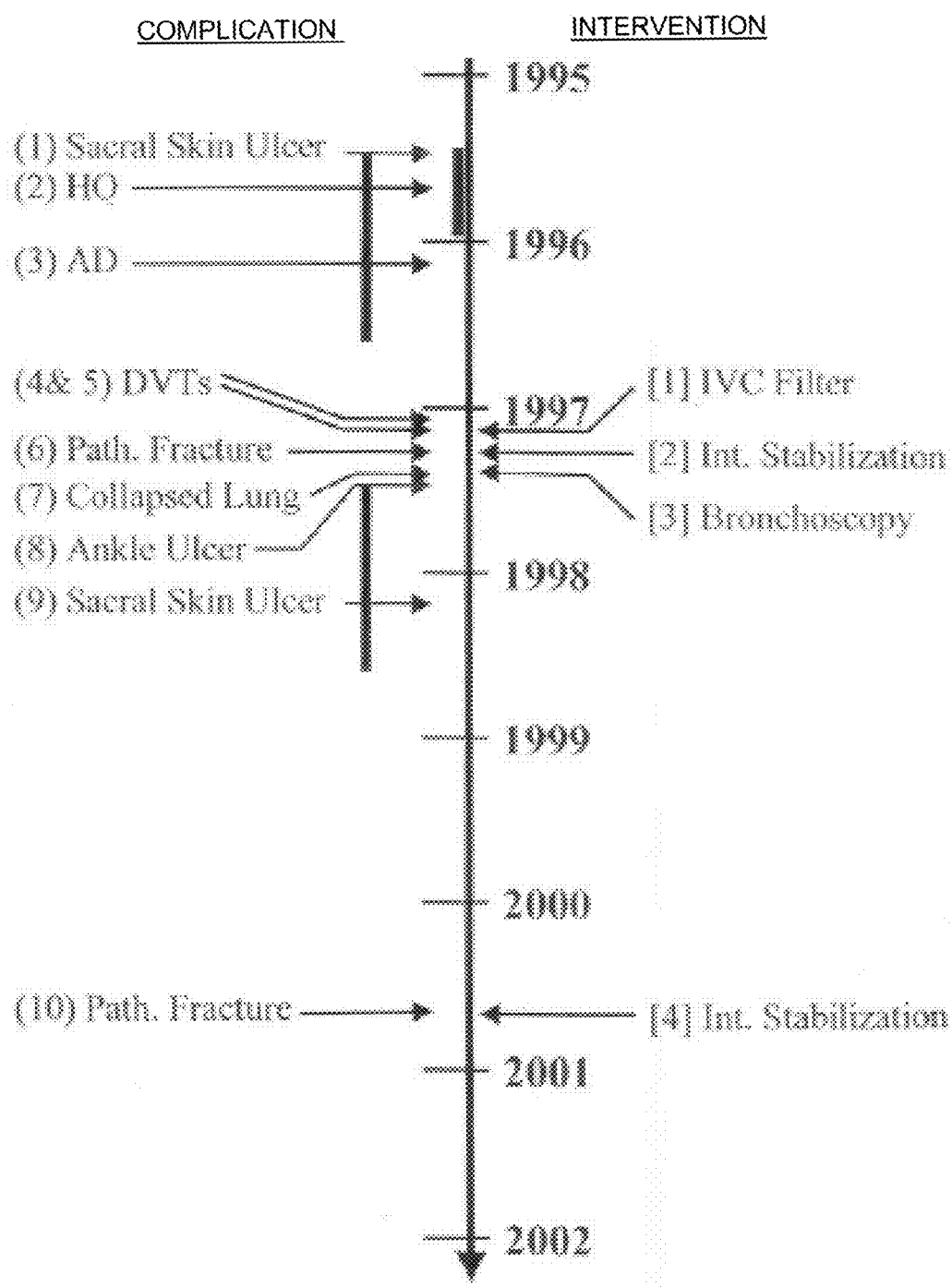
FIG. 4 is a schematic illustration of the timeline of injury and complications of the human patient of FIG. 3.

The Injury: FIG. 3 depicts serial T2-weighted MR images obtained in the patient's cervical spinal cord 5 years after the C-2 SCI. FIG. 3 shows a posttraumatic cyst at C-2 level and severe encephalomalacia in the patient who had suffered a traumatic SCI 5 years earlier. A sagittal MR image is shown on the left (A) and the corresponding coronal sections are shown the right (B-E). For ease of identification, the perimeter of the cord is circled in black and the internal cyst is white in panels C and E, which are duplicate images of panels B and D. Graph showing quantitative analysis of spinal cord area by using MR imaging signal. Areas (in $mm^2$) of the MR image signal in cross sections through the spinal cord are shown as a function of distance from the cerebellar tonsils (0 reference point). The lesion epicenter is indicated by the lowest point on the U-shaped area curve. Based on a normal C-2 cervical cross-sectional area of approximately 1 $cm^2$, then approximately 25% of the MR imaging signal remains at the injury epicenter, representing a donut-like rim of tissue. FIG. 4 is a schematic illustration of the timeline of injury and complications of the human patient.

The injury epicenter contains a central cyst on level with the lower part of the C-2 vertebral body. For ease of reference, the central cyst is shown in white in insets C and E. In the same insets, black lines outline the cord. As is typical in high cervical injuries, severe encephalomalacia (shrinkage) has almost halved the diameter of the upper cord. Despite the severe damage, cross sections through the lesion (horizontal lines with arrows pointing to insets B-E) indicate a variable donut-like rim of remaining white matter tissue. The presence of a variable donut-like rim of tissue at the injury site is typical of most SCIs. Furthermore, the majority of clinically important motor and sensory tracts are normally present in the outer rim of white matter; however, the MR images do not indicate whether the donut-like tissue is functional cord or simply scar tissue. An interesting feature of the patient's images is that the cystic area is confined to the C-2 level rather than extending one level above and below, as is more typical with traumatic SCI. The likely explanation is that the cervical canal is wider at C-2, which protects the cord more than the canal at other levels.

Quantitative measures of remaining spinal cord cross-sectional areas in the upper cervical region revealed that approximately 25 $mm^2$ of tissue remained at the lower C-2 lesion epicenter, representing a donut-like tissue rim (FIG. 3F). The lesion epicenter was identified by reduced average signal intensities with corresponding minimal area values. As suggested in the MR images, the area of the most severe injury was primarily confined to one level (labeled C-2 in FIG. 3F); however, substantial atrophy of the cord was also present rostral and caudal to the injury level. This atrophy extends further rostral than caudal in keeping with the greater rostral axonal dieback observed in high cervical lesions in rodents.

Examination: Examination was consistent with a complete motor and sensory quadriplegia. Cervical traction was instituted. He received methylprednisolone (30 mg/kg bolus, followed in 1 hour by 5.4 mg/kg) after the injury. Cervical spine x-ray films demonstrated a Type II odontoid fracture with fracture of the occipital condyle and displacement of the occiput anterior to C-1, suggesting occipitoatlantal dislocation.

The current case reinforces the data noted above that limited sparing of white matter may be associated with substantial preservation of motor and sensory function. In the patient's case, high-resolution MR imaging demonstrated that less than 25% of the cord had survived at the injury level (and the proportion was probably lower because MR imaging cannot distinguish between functional tissue and scar tissue). Yet substantial motor and sensory recovery was possible. These observations imply that small stepwise treatments can be expected to produce large gains in function. Development and application of novel methods for determining persistent connections across the lesion in individuals with ASIA Grade A injuries will be important. Such techniques could include diffusion tensor imaging, functional MR imaging, and motor/sensory evoked potentials.

The MR imaging analysis of the lesion indicated residual sparing of approximately 25 $mm^2$ of tissue in an outer donut-like rim of the cord at the C-2 level. The analysis would tend to err on the side of inflated area measurements, as the demarcation of tissue and cerebrospinal fluid in the central cyst was not always a clean border. Nonetheless, the lesion epicenter can be identified in FIG. 3 by a simultaneous drop in signal intensity and minimal residual area. Previous work in normal volunteers suggests the area of C2-4 spinal cord cross-sections ranges from 67 to 101 $mm^2$, with study means ranging from 78.1 to 84.7 $mm^2$. Previously published data obtained in normal human volunteers at the C2-3 and C3-4 disc space levels, based on MR imaging, is as follows: mean age 31 years (range 23-49 years), area 78.1 $mm^2$ (range 70.1-86.1 $mm^2$) for 15 volunteers; mean age 38 years (range 26-57 years), area 84.7 $mm^2$ (range 67-101 $mm^2$) for 30 volunteers. Therefore, it is reasonable to assume that approximately 25% of the cord remains at the injury level in the patient.

Operation and Immediate Postoperative Course: Nine days later occiput-C2 fusion was performed (FIG. 1) using a titanium ring and sublaminar soft wire at C-1 and C-2. Bone was obtained from the iliac crest. Because the MR imaging appearance was consistent with preserved neural tissue, great care was taken to maintain alignment during the procedure and in particular when turning the patient from supine to prone.

As is usual in high cervical injuries, the patient underwent tracheostomy and gastric tube placement. All the early ASIA examinations for SCI demonstrated similar results. For example, the examination on Jun. 24, 1995, almost 1 month after the injury, indicated a classification of ASIA Grade A, with complete motor and sensory function at level C-2, partial preservation of sensory function at C-3, and spotty sensation in the left hemibody, this level including absence of sacral function such as voluntary anal contraction. The patient received a single test dose of GM-1 ganglioside 39 days after injury, but mastocytosis precluded further doses. The patient's initial hospital course, including inpatient rehabilitation, was uncomplicated except by sacral skin breakdown (Grade IV that healed by secondary intention). When the patient was discharged from the hospital on Dec. 13, 1995, approximately 5 months after the injury, he was dependent on a ventilator and his SCI was classified as C-2 ASIA Grade A.

Long-Term Treatment Course:

1. Informed Consent and Approval. The Human Studies Committee at Washington University in St. Louis approved the methods for collecting data and presenting the case. Informed consent was obtained for participation in research activities in accordance with this committee's standards from the individual described herein. Inclusion of the quality of life questions and answers were approved by the patient.

2. The "N of 1" Study Design. The "N of 1" analytical method is an accepted rational design that has attracted interest from the National Institutes of Health.

3. The ASIA Examinations. The ASIA examinations spanning the period prior to recovery (1999) through recovery (end 1999-2002) were performed in accordance with ASIA's International Standards by a single investigator (J.W.M.) trained in the measurements and in the specialty of SCI medicine. The results of early examinations were obtained from ASIA sheets in the original hospital charts (1995-1999). The individuals who performed these examinations were also experts in SCI care and well versed in the clinical ASIA standard examination. Initial examinations by the serial examiner (J.W.M.) confirmed these earlier records (1999). All components of the examination were performed in accordance with ASIA standards while the individual was lying in bed. The ASIA International Standard test for patients with complete tetraplegia has good intra- and interrater reliability.

4. Electromyography Evaluation. The Advantage/Clarke-Davis (diaphragm) and Dantec/Keypoint (upper and lower extremity muscles and external sphincter muscle) instruments and a Medtronic disposable monopolar needle DMN 50 were used for electromyography. Amplifier input impedance was set at 5 kOhm, with a high-pass filter of 2 Hz, a low-pass filter of 10 kHz, a sweep of 10 to 200 msec/D and a sensitivity of 0.1 to 0.2 mV/D. The diaphragm was evaluated while the patient was seated, and the following muscles were assessed while the patient was lying down: right deltoid, biceps, extensor carpi radialis, and vastus medialis.

5. Bone Density. Bone densitometry was performed at Washington University School of Medicine's Bone and Mineral Diseases laboratories. Dual-energy x-ray absorptiometry measurements were compared using national standards for white males (based on age, weight, and height). Data are presented as standard deviations using t-scores (sex-matched normal young adult reference).

6. Magnetic Resonance Imaging

Safety Testing:

Before placing the patient in the MRI scanner, duplicate copies of the orthopedic instrumentation were acquired for testing of MR compatibility. To simulate the titanium loop instrumentation in the patient's cervical region (Danek Inc., Minneapolis, Minn.), two stainless-steel Harrington rods and stainless steel circlage wires were obtained for testing. A neurosurgeon bent the rods using a standard bending apparatus to approximate the bend of the straight segments of the patient's Danek loop, using the patient's plain-film radiographs. This bending was performed because stainless steel could become slightly magnetic when bent.

The rods and wires were manually passed in and out of the MRI scanner. No torques were felt on the metal that would indicate any force due to magnetic properties. A strong hand-held magnet was also moved around the metal, and no attractive forces were felt. The rods and wires were then arranged to match the configuration on the radiographs. The hardware was taped to a spherical phantom containing 0.9% NaCl (saline) and doped with 0.15 mM Gd[DTPA-BMEA] (Optimark, Mallinckrodt Inc., St. Louis, Mo.) to shorten the T1 relaxation time to the physiological range. The phantom was placed in the MRI scanner, and several scans were performed using various pulse sequences that were planned to use in subsequent patient imaging sessions (MP-RAGE, turbo spin echo, echo-planar imaging, diffusion tensor imaging, etc.).

The investigator held his hand over the metal during the imaging, and did not feel any RF heating or movement of the metal.

Patient setup: The patient was transported to the MRI suite by van, and all external metal was removed from his pockets. During transport and MRI the patient was ventilated using his personal ventilator connected to a tracheostomy tube for positive ventilator assistance. Outside the MRI room, the patient and his ventilator were moved onto a lightweight aluminum stretcher (Model 30NM, Ferno-Washington Inc., Wilmington, Ohio) tested for MR-compatibility, and then the patient was transported into the MRI room. A pulse oximeter probe was placed on his right index finger to monitor heart rate and oxygen saturation (using a rubber grip sensor, Invivo Research, Inc., Orlando, Fla.). A non-invasive blood pressure cuff was placed over the left arm and a tubing was connected to a side-port of the ventilator connector to monitor blood pressure, respiratory rate, end-tidal $CO_2$, and inspired O2 (3150 Magnitude/3155A Millenium anesthesia monitoring system, Invivo Research, Inc., Orland, Fla.). The ventilator tubing was temporarily disconnected and the patient was lifted onto the MRI table. The ventilator tubing was immediately reconnected, and a wall $O_2$ line was connected to the ventilator (medical grade $O_2$, Airgas, St. Louis, Mo.). The oxygen flow was adjusted to 2-3 L/minute to maintain SpO2 to >95% in the supine position. (In the upright position the patient typically has an $SpO_2$ of 97-98% without additional $O_2$.) The patient was positioned so that the C2-C3 region of the cervical spin was centered over the active element of the neck phased array coil (see below). Padding was placed under the elbows, knees, and back. The ventilator and $O_2$ line were temporarily disconnected and moved to inside a non-magnetic RF-shielded box (Shielding Resources Group, Tulsa, Okla.) placed next to the MRI scanner. The RF box contained a shielded AC/DC power source, shielded electronic connectors, and waveguides (copper conduits) built into the walls of the box. The ventilator and $O_2$ tubings were fed through a waveguide and reconnected to the ventilator inside the RF box. This RF box was tested at >80 dB attenuation to completely screen RF emissions from the ventilator and remove severe RF interference in the MRI. Headphones were placed on the patient for acoustic shielding and listening to music, and tape was placed across the forehead to minimize movement of the head and neck. The patient was then advanced into the scanner by moving the patient table, positioning the C2-C3 region and active coil element at the isocenter of the magnet and gradients. The display from the Invivo monitor was then connected from a custom video port of the Millenium 3155A anesthesia unit through a custom RF penetration panel in the MRI room wall (Shielding Resources Group, Tulsa, Okla.) and then to the back of the satellite MR console monitor for display of physiologic data in the control room, where a neurointensivist monitored all physiologic parameters during MRI. During the entire setup and imaging period, the heart rate was 58-86 beats per minute, $SpO_2$ was 95-97%, blood pressure was 126-139 mm/72-86 mm, the respiratory rate was 18 respirations per minute (equal to the ventilator setting), the end-tidal $CO_2$ was 29-34 mm Hg, and the inspired $O_2$ (FiO2) was 28%. The patient did not experience any adverse symptoms during the imaging sessions.

MRI Acquisitions: A 1.5-Tesla Siemens Magnetom Vision MRI scanner and Siemens phased-array spine coil were used for all imaging (Siemens, Erlangen, Germany). After an initial scout to confirm positioning at the isocenter, the external magnetic field was shimmed manually using the vendor MAP-shim procedure. For this purpose, only the linear shim channels were used because of instability in the higher-order shim channels due to the adjacent metal instrumentation. The frequency and transmitter were then tuned to the on-resonant and 180° conditions, and the scout scan was repeated. A T1-weighted MP-RAGE scan was acquired next in the transverse plane, tilted ~20° sagittally and coronally to be perpendicular to the cord. The scan had 1.0-mm isotropic voxels (256×256 mm field of view and 256×256 matrix, 160-mm z-slab with 160 z-partitions) with TE=4.0 ms, TR=9.7 ms, TI (inversion time)=472 ms, and a 12° tip angle. The acquisition time was 9 min 29 sec with no signal averaging. The MP-RAGE data was used for cord cross-sectional area measurements (see below). Additional anatomical scans such as T2-weighted turbo spin echo and fluid-attenuated turbo inversion recovery were also acquired.

Data analysis: MP-RAGE data were resliced to be perpendicular to the cervical cord. Region-of-interest (ROI) tracings were made around the border of the cord on every other transverse image using the "auto trace" function of Analyze AVW 4.0 (Mayo Foundation, Rochester, Minn.). To choose the intensity level for the auto-trace, the lower level was determined in which the trace expanded out into the surrounding background noise, the higher level was determined in which the trace collapsed into the center of the cord. Then, the mean of the two levels was calculated and chosen for the auto-trace of the cord area. By this procedure, partial volume effects were taken into account in which the cord intensity transitions from high T1-weighted intensity to the low signal surrounding the cord (see FIG. 3). In some slices, the ROI generated by the auto-trace procedure had to be edited to prevent the region from extending into adjacent tissues (e.g., due to cord adhesions). The two-dimensional areas of the cord were measured by sampling the ROIs, and results were graphed as a function of length along the cord.

7. Quantification of Infectious Complications. The personal 24-hour nursing records for the patient were exceptionally detailed and this allowed us to track accurately the number and types of infections requiring antibiotic treatments each year. In addition, the total duration of each treatment was always recorded. The prescription records provided by the local medical doctor verified these values. In most cases, cultures were also obtained to further verify the infection.

8. Quality of Life Evaluations. A single examiner (J.W.M.) performed the evaluations by telephone (Jul. 15-30, 2002). These subjective measurements supplemented the quantitative data on functional recovery and emphasized the impact of limited motor and sensory recovery on quality of life.

9. Activity-Based Recovery Program. The activity-based recovery program consisted primarily of training on a FES bicycle. The customized recumbent bike system, designed for use with paralyzed individuals, integrated computer-assisted FES-induced cycling. The goal was 1 hour of activity (up to 3000 revolutions) per day three times per week. The FES bicycle modulates the intensity of stimulation to obtain a consistent rotation speed. Surface electrodes stimulate three muscle groups in each leg (FIG. 2): one electrode is placed at the superior edge of the gluteal muscle, another over the hamstring group midway between the knee and hip, and two over the quadriceps (one over the superior portion and the other over the inferior third of the quadriceps). During the exercise, the legs were balanced in three ways. The seated buttocks and boots anchored the legs at the upper and lower positions. Belts that attached to the upper leg with Velcro balanced the mid-leg. A weighted fly-wheel ensured a smooth rotation by carrying momentum. The goal was to achieve the greatest number of revolutions (3000/hour). The FES bicycle therapy was supplemented with surface electrical stimulation to activate the following muscle groups: paraspinals, abdominals, wrist extensors, wrist flexors, deltoids, biceps, and triceps. The therapies were rotated daily, usually in a 3-day sequence. Each muscle group was activated for half an hour using intermittent 1 second on, 1 second off AC cycles. Once muscle recovery began, aquatherapy was incorporated into the program, with a goal of one 1-hour session per week. The aquatherapy focused on muscle groups in which voluntary control was recovered while participating in the activity based recovery program.

Upon first evaluating the patient, the activity-based recovery program's effects on physical as well as functional recovery was studied. Early results suggested that the physical benefits alone were sufficient reason to incorporate activity-based therapy into daily life. Those benefits included enhancement of muscle mass and bone density, increased cardiovascular endurance, and decreased spasticity (data not shown).

After the initial evaluation at Washington University in St. Louis, the patient was trained to use a FES bicycle (FIG. 2). A similar bicycle was installed in his home so he could exercise frequently in his city of residence. The goal was to complete a 1-hour session three times per week.

At first, the patient's leg muscles fatigued rapidly with surface stimulation, but within approximately 20 sessions he was able to ride the bicycle continuously for 1 hour. Once motor recovery began, the program was supplemented with weekly aquatherapy to work muscle groups that had regained voluntary function but were too weak to oppose gravity. Surface, non-load bearing electrical stimulation was also performed on the following muscle groups on an alternating 3-day schedule: the paraspinal group, the abdominal group, and the upper-extremity groups. Standard range-of-motion physical therapy was also performed daily, but this regimen was not changed from the time the individual was first discharged from rehabilitation. Breathing exercises also became part of the daily routine beginning in 1998. Increased muscle size and a generalized improvement in health were clearly evident by the year 2000; however functional recovery was slower.

1. Major Medical Complications. As usually happens with a high cervical SCI, the patient developed many severe medical complications, particularly between 1996 and 1999 (FIG. 4). The patient suffered a C-2 ASIA Grade A SCI on May 27, 1995. As often happens in tetraplegia, he accumulated many severe medical complications, which are listed in this timeline. The vertical red bar indicates inpatient medical care and rehabilitation through the end of 1996. In addition to the complications shown here, urinary tract and pulmonary infections were frequent in the years before 1999. Note that the complication rate accelerated between 1995 and 1999, a situation common in tetraplegia. The paucity of similar complications after 1999 is highly unusual. 1) Coccyx skin ulcer. A large, Grade IV sacral skin ulceration developed early during the hospitalization period. Aggressive treatment produced healing by secondary intention 1 year later (the vertical green bar indicates healing time). 2) HO. Heterotopic ossification (lesser trochanter of right femur) developed in July 1995, as indicated by acute swelling of the right thigh. A Doppler study was negative for deep venous thrombosis, and x-ray films and CT scanning failed to reveal a fracture. Treatment with Didronel was initiated to prevent further bone resorption. Heterotopic ossification is a common complication in the acute postinjury period. 3) AD. Severe autonomic dysreflexia required inpatient treatment. 4 & 5) DVTs. Left deep venous thrombosis occluded the large draining vein of the leg and required hospitalization for anticoagulation with heparin and then Coumadin. The DVT recurred 1 month later, requiring adjustment of the anticoagulation regimen and placement of an inferior vena cava (IVC) Greenfield filter. Life-long treatment with Coumadin and weekly blood anticoagulation testing was then required. 6) Pathological fracture. Pathological fracture of the left femur resulted from a low fall during transfer. Surgical intervention was required to stabilize the fractured bone. 7) Collapsed lung. Acute shortness of breath required emergency hospitalization and bronchoscopy to remove a mucous plug. 8) Ankle ulcer. A left lateral malleolus skin ulceration (Grade IV) was complicated by slow healing and osteomyelitis, threatening amputation. Aggressive treatment and healing by secondary intention took more than 1 year. 9) Sacral skin ulcer. Pilonidal cyst removal and suture closure was complicated by dehiscence and development of a sacral wound that required aggressive treatment and healing by secondary intention (vertical green bar indicates healing time). 10) Pathological fracture. The left femur fractured while the patient was attempting weight-supported standing. Treatment required hospitalization and surgical internal fixation. Additional treatment of severe osteoporosis included vitamin D, calcium supplements, and pharmacological treatment to limit bone resorption.

Despite his severe injury and immobility, however, he fared extremely well. These complications included skin breakdown, heterotopic ossification, autonomic dysreflexia, pathological bone fractures, deep venous thrombosis, and acute respiratory distress consequent to mucous plugging.

Figure 5:
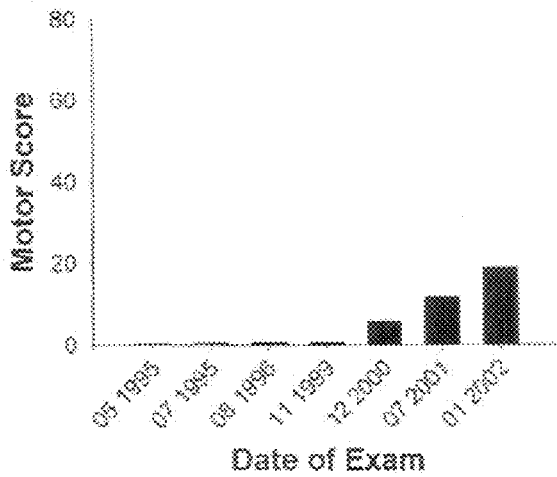
FIG. 5 displays graphs describing marked recovery of the human patient from SCI.
Figure 5:
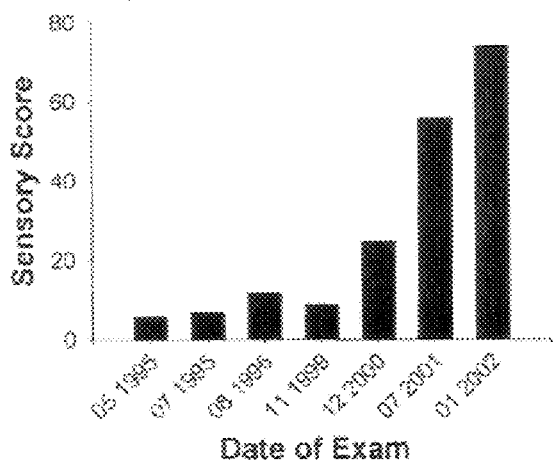
Figure 5:
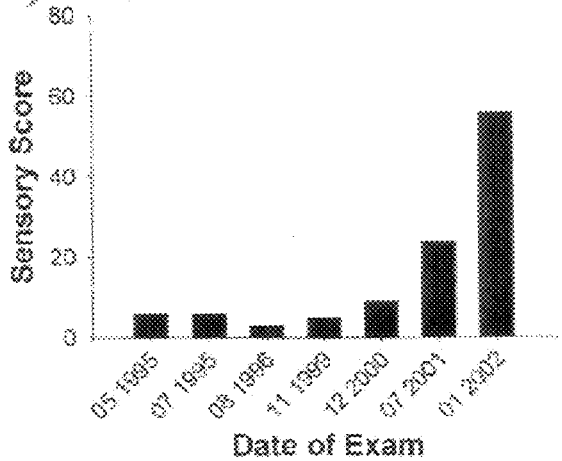

2. Recovery of Function. The patient experienced no functional improvement during the first 5 years after injury, thereby retaining the C-2 ASIA Grade A classification, and the likelihood of any substantial improvement in the following years seemed negligible. Multiple ASIA examinations during the first 5 years after the patient's injury documented a lack of substantial motor or sensory function because motor scores were consistently 0/100 and sensory scores ranged from 5-7/112. The first ASIA examination at Washington University in 1999 was consistent with these observations. FIG. 5 shows graphs quantifying the marked recovery from SCI. Data are presented as parameter values (x-axis) and total motor and sensory function (light touch, pinprick; y-axis) based on the international ASIA standard scale for rating severity of SCI.

Motor function was assessed in five myotomes in the arms and five myotomes in the legs, and the scale of 0 to 5 provided a maximum score of 100 (10 muscles on each side). Sensation was measured in 28 dermatomes on each side. The scale of 0 to 2 (0=absent, 1=impaired, 2=normal) provided a maximum score of 112. The ASIA classification runs from Grade A to E, with E being normal. This individual displayed no motor function during the first 5 years after injury. Sensory function over the first 5 years was restricted to upper neck dermatomes. The activity-based recovery program was instituted mid-1999. After 6 months, no recovery was observed; however, progressive and considerable motor and sensory recovery was evident over the next 2.5 years.

The patient did begin to recover sensation to deep palpation in the upper torso and upper arms in early 1999, but this did not translate into substantial changes in the ASIA grade because since detection of light touch and pinprick sensation are the only measures.

After the first 6 months of the activity-based recovery program (January 2000), little recovery of function was evident: the arms and legs still displayed no motor function and a light touch or pinprick could be sensed only above the affected dermatomes in the neck (C1-C2/3). The patient first noted the ability to control a twitching movement of his left index finger in early November 2000. The first documented recovery on ASIA examination was at the end of 2000 (FIG. 5). Although modest improvements in sensory and motor scores were observed, sacral sparing of light touch sensation was first evident, changing the patient's ASIA classification to ASIA Grade B. Twenty-two months into the program (July 2001), however, light touch sensation improved to 52% of normal. It recovered to 66% of normal in 2002. Pinprick assessment, which requires discrimination and is therefore more difficult, did not improve until the last year of the 3-year program, which is ongoing to date. Sensation was appreciable throughout most dermatomes of the body (FIG. 6), including the sacral region (S-3, S4-5). In addition to recovery of pinprick and light touch, recovery of additional sensory modalities occurred and included vibration, proprioception, and ability to differentiate heat and cold.

Figure 6:
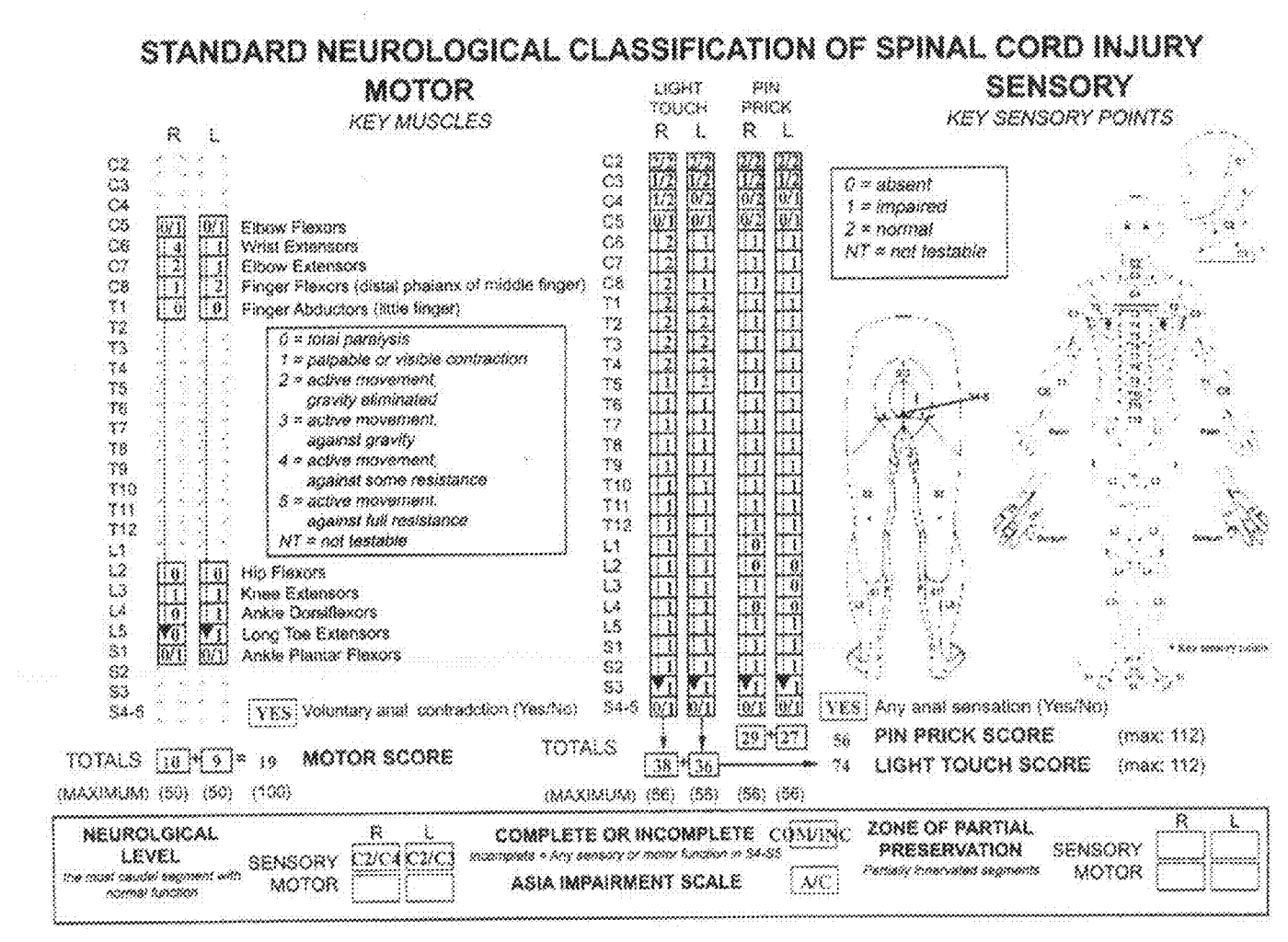

The most notable change was an improvement in motor function of up to 20% (20/100). Voluntary control of the external anal sphincter is possible (S4-5). The conversion of the patient's condition to ASIA Grade C thus occurred in July 2001. Motor recovery was first evident in the left fingers, then the right hand, and then the legs. Movement is now possible for most muscles of the upper arms but for fewer muscles in the legs. Most muscles in the legs are not yet able to oppose gravity. FIG. 6 is a schematic drawing showing a comparison of the patient's ASIA grades from 1995 to 2002. Values in blue indicate scores from 1999; those in red indicate 2002 scores. Note that all the 1995 motor scores and the sensory scores obtained below T-4 were zero. The 1995 scores were taken from the July 1995 ASIA sheet.

The following comparison puts this motor recovery into perspective. The National Acute Spinal Cord Injury Study II and III trials documented an average 4.8-point improvement in the motor scores of patients receiving methylprednisolone compared with those receiving placebo if methylprednisolone was given within 8 hours of injury.

In the patient's case, there was a 20-point improvement in motor score over Years 5 to 8 post-injury (FIG. 5), which translates into movement in most joints, including the elbows, wrist, fingers, hips, and knees (FIG. 6); thus, the patient's condition is now categorized as ASIA Grade C rather than Grade A. This degree of movement gives the patient better control of the environment and of his powered wheelchair. The direct consequences of the recovered movement are limited but the consequences of the sensory recovery are substantial. In addition, the other benefits associated with enhanced muscle function have tremendously improved the patient's quality of life.

3. Reduction of Infections and Physical Improvements. Strikingly, the patient's infection complication rate began to decline dramatically in 1999, in parallel to reductions in major complications and recovery of neurological improvements. The incidence of infections requiring antibiotic treatment and total days of antibiotics per year also dramatically improved following 1999. Evaluation of total days of antibiotics required revealed over a 90% reduction in Years 2000 to 2002 compared with Years 1996 to 1998 (Table 2).

TABLE 2

Yearly Incidence of Infections and Requirement for Antibiotic Treatment

| Year | Total events requiring antibiotic treatment | Urinary tract infections | Pulmonary infections | Bowel infections | Skin infections | Total days of antibiotic treatment |
|---|---|---|---|---|---|---|
| 1996 | 23 | 10 | 9 | 3 | 1 | 169 |
| 1997 | 13 | 4 | 4 | 0 | 4 | 190 |
| 1998 | 13 | 5 | 6 | 0 | 2 | 168 |
| 1999 | 8 | 1 | 4 | 0 | 3 | 99 |
| 2000 | 5 | 3 | 2 | 0 | 0 | 36 |
| 2001 | 3 | 3 | 0 | 0 | 0 | 18 |
| 2002 | 1 | 1 | 0 | 0 | 0 | 10 |

Events were recorded from detailed personal nursing records and indicate total number of infectious events requiring antibiotic treatment, types of infections and total days of antibiotic treatment required.

In addition to these improvements, the patient also achieved substantial physical benefits. His severe osteoporosis, which contributed to pathological fractures of two of the largest bones in his body (femur and humerus), was completely reversed and is now within the normal range (bone density t-score −0.5 in 2002 compared with −4.1 pre-1999). Ashworth measurements of spasticity have improved from 3 to 1-2 (Table 3), and the patient has also increased his endurance.

TABLE 3

Ashworth Scale for Measuring Spasticity

| Ashworth Score | Degree of Muscle Tone |
|---|---|
| 1 | No increase in tone |
| 2 | Slight increase in tone resulting in a "catch" when affected limb is moved in flexion and extension |
| 3 | More marked increase in tone; passive movement difficult |
| 4 | Considerable increase in tone; passive movement difficult |
| 5 | Affected part rigid in flexion and extension |

4. Electromyography Results. The EMG analysis of volitional movements was completed in the winter of 2001 (Table 4), and the results were compared with those from phrenic nerve testing performed on Jun. 21, 1995, shortly after the injury. At that time, there was evidence of intact anterior horn cells. Latencies were less than 10 msec, and right and left amplitudes were 0.9 mV and 0.5 mV, respectively. Diaphragmatic movement, albeit small, was noted on fluoroscopic examination. In contrast, amplitudes were greater in 2001 (2-7 mV), but there was further evidence of denervation (Table 4). Voluntary elicited EMG responses were evident in other muscle groups tested, including the right deltoid, right biceps, right extensor carpi radialis, and right vastus medialis. Most of these groups showed evidence of denervation, as indicated by positive sharp waves, fibrillation, and complex repetitive discharges. Overall, the numbers of recruited motor units were predictably small.

TABLE 4

EMG Characteristics of Muscles During Volitional Activation

| Muscle group | Voluntary response | Response latency (ms) | # Motor units recruited | Insertional activity | Spontaneous activity (PSW, Fibs, CRDs) | Motor unit characteristics | | |
|---|---|---|---|---|---|---|---|---|
| | | | | | | Amplitude (mV) | Duration (ms) | Configuration |
| L. diaphragm | No | NA | 1-2 | No | No | 2 | 5 | NL |
| R. diaphragm | Yes | NA | 3-4 | No | No | 2-7 | 5-20 | NL |
| R. deltoid | Yes | 180 | 1 | Yes | PSW, fibs | 0.7 | 5 | polyphasic |
| R. biceps | No | NA | NA | Yes | PSW, fibs | NA | NA | NA |
| R. extensor carpi radialis | Yes | <200 | 2 | Yes | PSW, fibs, CRD | 1.5-2 | 5 | polyphasic |
| R. vastus medialis | Yes | 200-500 | 1-2 | Yes | PSW, fibs | 1.5-2 | 4 | NL |

EMG characteristics of key muscles in response to commands to voluntarily move the muscle group. Columns indicate muscle groups recorded, presence of identifiable EMG response to activation request (voluntary response), delay in EMG activation compared to voluntary activation request (Response latency), number of motor units recruited with increasing effort to move (# Motor units recruited), presence of activity with insertion of the EMG needle (Insertional activity), presence of spontaneous resting activity (Spontaneous activity), and characteristics of motor units (Motor unit characteristics: Amplitude, Duration, and Configuration). Abbreviations: positive sharp waves (PSW); fibrillations (fibs); complex repetitive discharge (CRD); normal (NL); not assessed (NA); millivolts (mV); millisecond (ms).

5. Quality of Life Assessment. Table 5 lists the responses the patient made in 2002 to questions about quality of life. Overall, recovery impacted many domains of daily living, but the changes perceived as life-altering were: avoidance of sickness and sick days; improved ability to anticipate stable health and the ability to fulfill work and family obligations; improved health; improved weight control; more attainable life goals; improved ability to breathe without a ventilator; positive impact on the family; greatly improved economics because of reduced medical costs, fewer lost work days; enjoyment of being healthier; greater enjoyment of leisure activities; improved productivity; knowledge that progress had replaced regression; less spasticity; and greater hope for additional recovery. The semi-quantitative quality-of-life measures that are available because of their limited ability to detect the impact of such a recovery.

Example 2

CNS Regeneration in Rats

Subjects, animal care and surgery: Thirty adult Long Evans female rats (275±25 g; Simonsen, Gilroy, Calif.) were housed (12:12 h light:dark cycle) and treated in accordance with the Laboratory Animal Welfare Act, and Guidelines/Policies for Rodent Survival Surgery (Animal Studies Committee of Washington University in St. Louis).

Figure 7:
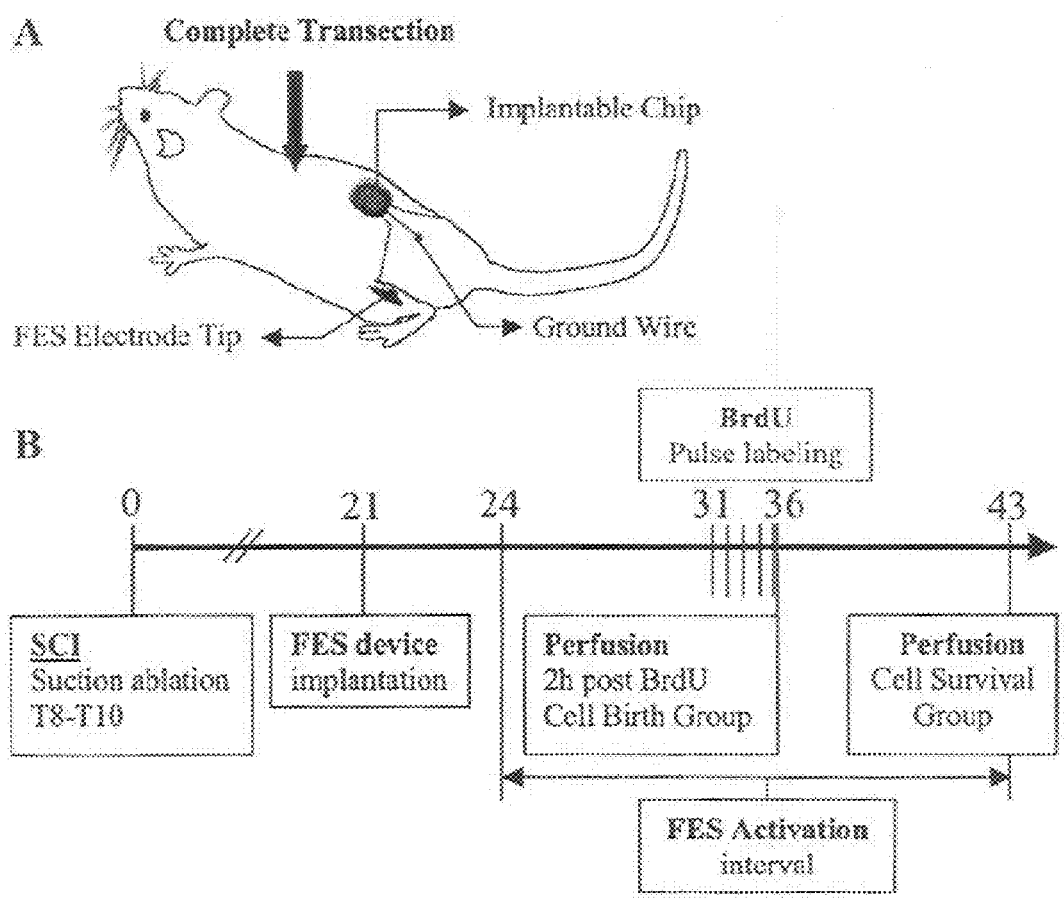
FIG. 7(a) schematically illustrates the methodology used in a rat model of spinal cord injury to evaluate the effects of FES-evoked patterned movement.
FIG. 7(b) is a time line of the experimental design for the rat model of spinal cord injury.

Six groups were examined using two survival intervals following the BrdU pulse label, either immediate or 7 days later. All 30 rats received FES implants. Twenty-four rats received a spinal cord injury 3 weeks prior to FES device implantation. Six additional rats were uninjured controls. In half the animals (n=15) the FES systems were activated. FIG. 7(a) shows a schematic drawing of the experimental rat model showing the relationship between the injury and stimulation level.

FIG. 7(b) shows the 43-day time line for the experiment in which twelve Long Evans adult female rats received a complete transection of the spinal cord by suction ablation of two levels (T8-9). To simulate a chronic type of injury we waited three weeks before the FES devices were implanted. Following a three-day post-surgical interval the devices in half of the rats were activated for 3 hours per day for 12 days. Between day 7 and day 12 of the FES schedule, we conducted a daily BrdU pulse labeling protocol. Two hours after the last BrdU injection all rats were sacrificed.

Bladders were expressed 3 times daily until recovery of reflex emptying. To prevent autophagia, rats were fitted with 10.5 cm plastic collars (Ejay, Glendora, Calif.), and housed individually with absorbent bedding (ALPHA-Dri™, Shepherd, Kalamazoo, Mich.) and nesting material. Individuals blinded to the treatment, and independent of the surgical team handled each rat for 5 min each day.

Spinal cord injury: Rats were anesthetized (75 mg/kg Ketaset®, 0.5 mg/kg Domitor®, i.p.), and a laminectomy was done at T7-T9. Through a 1 mm dura incision, 1 mm of the spinal cord was removed under microscopic control via suction utilizing a BARON® suction tube (Roboz, Rockville, Md.). The dural opening was covered with fascia and the muscle and overlying skin closed with layered sutures. Anesthesia was reversed by Antisedan® 1 mg/kg. This method of suction ablation minimized bleeding compared to surgical blade transection, maintained the integrity of the dura and major blood vessels, and resulted in clean cord wound borders.

Stimulator and electrode implantation: Three weeks following SCI the rats were re-anesthetized, a midline incision was made over the lower back and a 2-channel battery powered electrical stimulator (Jarvis, University of Liverpool) and current return electrode were implanted in a subcutaneous pocket. A 0.5 cm incision was made on the lateral aspect of both shanks and stainless steel wire electrodes were tunneled bilaterally underneath the skin from the stimulator site, and sutured into the tibialis anterior muscle adjacent to the common peroneal nerve. Intra-operative test stimulation ensured proper peroneal nerve activation.

Electrical stimulation paradigm: FES devices were activated daily for 19 days between 24 and 43 days after injury (starting at 3 days following implantation), for three 1 h sessions during each 9 h workday (FIG. 11B). An additional group of 6 rats received the identical FES implant and activation pattern but were not injured. The pattern of stimulation was 1 s stimulation of one common peroneal nerve, followed by 1 s of rest, then the other common peroneal nerve was stimulated for 1 s, followed by 1 s of rest and the cycle repeated. Stimuli were 3 V 200 μs monophasic pulses delivered at 20 Hz between the electrode over the nerve and the return electrode in the lower back and were expected to activate large myelinated fibers within the common peroneal nerve, but not small unmyelinated nociceptive fibers. The nerve stimulation produced alternating flexion of the hindlimbs that crudely approximated bilateral stepping-like hindlimb movements.

Bromodeoxyuridine injection paradigm: Newborn cells were identified by daily injections, beginning day 31-36 after injury, with BrdU (50 mg/kg i.p.), a brominated DNA building block that is selectively incorporated into replicating DNA during the S phase of the cell cycle.

Tissue processing: Two hours after the final BrdU injection, half of the rats (n=15) were deeply anesthetized and perfused intracardially with 0.1 M PBS for 5 min followed by 4% paraformaldehyde (Sigma) for 15 min. One week after the final BrdU injection the remaining rats were sacrificed (n=15).

Immunohistochemistry: Every 6th section (40 μm) from spinal cord levels C2, T1, T7, T11, L1, and L5 was selected for anti-BrdU immunohistochemistry. Sections were incubated in 2 N HCl for 60 min at 37° C., transferred to 0.1 M Borate buffer (pH 8.5) for 20 min, and rinsed with PBS. Non-specific labeling was blocked with 0.1% BSA in 0.1% Triton X-100/PBS for 60 min. A mouse monoclonal anti-BrdU antibody (1:600; Roche, Mannheim, Germany) was incubated with the tissue overnight at 4° C. Then tissue was treated with a CY3-conjugated secondary antibody (1:2000; Jackson, West Grove, Pa.) in 2% normal goat serum (NGS) for 60 min.

For co-labeling of the BrdU positive cells, sections were fixed with 4% paraformaldhyde for 30 min after the CY3-conjugated antibody was applied. They were then permeabilized when appropriate with 0.1% Triton-X-100 for 60 min, and blocked with 2% NGS for 60 min. Primary antibodies diluted in 2% NGS were applied to the sections for 2 hours. Antibodies used included: rabbit anti-NG2 (1:250, Chemicon, Temecula, Calif.), mouse anti-Nestin (1:8, Developmental Studies Hybridoma Bank—DSHB), rabbit anti-GFAP (1:4, Diasorin, Stillwater, Minn.), mouse anti-APC-CC1 (1:20, Oncogene, Cambridge, Mass.), mouse anti-ED1 (1:100, Serotec, Raleigh, N.C.), mouse anti-OX42 (1:100, Serotec), sheep anti-Glut-1 (1:30, Biodesign, Saco, Minn.), rat anti-CD31 (1:20, BD Pharmingen, Lexington, Ky.), mouse anti-NeuN (1:200, Chemicon), mouse anti-TUJ1 (1:200, Babco, Richmond, Calif.), guinea pig anti-doublecortin (1:3000, Chemicon), and mouse anti-PSA-NCAM (1:8, DSHB). Secondary antibodies (1:300, Molecular Probes, Eugene, Oreg.) were conjugated to Alexa 488. Primary and secondary control slides were included with each stain series.

Quantification of BrdU positive cells: The number of BrdU-labeled cells as a function of spinal cord level was measured in a blinded fashion. Images were acquired on an Olympus IX70 Microscope equipped with a Magnafire® camera and quantitative counts were performed using a computer assisted software package (Stereoinvestigator™, Microbrightfield Inc., VT). For unbiased stereological counts of proliferating cells the indicator fractionator method was used. The estimate of BrdU positive nuclei was based on counts of nuclei in a known fraction of the volume of the region under consideration. A labeling index was calculated by taking the total number of BrdU positive nuclei per volume and dividing it by the total number of Hoechst 33342 (Molecular Probes) labeled nuclei per volume acquired from corresponding spinal cord sections. Sections were viewed under 200×, and systematically scanned by moving in a raster pattern with the aid of a mechanical stage (Ludl, Hawthorne, N.Y.). Stereoinvestigator™ software superimposed a sampling grid with an unbiased counting frame (x=122 m, y=110.1 m) on the image. The sampling frame was focused through the section at a known distance and BrdU positive nuclei were marked inside the counting frames. Based on these markers, area measurements, and defined volumes, the software calculated the total number of BrdU positive nuclei. To determine the phenotype, cells were evaluated for colabeling with each phenotypic marker. For each BrdU positive cell, the complete cell nucleus was followed through the z-axis, and only cells with a well-circumscribed immunopositive cell body were considered positive for a particular phenotype.

Statistical analysis: Comparison between experimental groups was conducted by two-way ANOVA using SigmaStat® applying Tukey post-hoc tests. Comparisons were made for the total number of BrdU positive cells and phenotypic markers between groups and within groups by spinal cord level. For all statistical analyses significance was accepted at $p<0.05$ with Bonferroni correction for multiple tests.

FES Increased the Number of BrdU Positive Cells Below the Level of Injury

FES produced a substantial increase in the density of new cell birth/survival at the lumbar levels of the spinal cord, consistent with a robust projection of the peroneal nerve to the lumbar spinal cord. The rostral-caudal selectivity of the effects of FES-induced hindlimb locomotion on cell birth/survival helps exclude possible global mechanisms such as metabolism, blood borne and other systemic factors, and strengthens support for local mechanisms associated with increased neural activity. Electrical fields in the range of 300 V/m can induce changes in neural cell function. Based upon the 100× larger magnitude of electric field required to produce direct effects in other studies, compared to the very small electric field experience by the spinal cord in these studies (about 5 V/m), the neuronal activity rather than direct electric field effects is demonstrated to be responsible for the observed effects.

The rat spinal cord was completely transected by suction ablation at T8/T9 to minimize intra-animal variability that might occur with less complete lesions, but this model limited analysis of functional recovery. Previous studies indicate that thoracic separation of the spinal cord produces reduced neural activity below the lesion level and that peripheral nerve stimulation or gait activity enhances activity at the respective cord level. A chronic injury was chosen because it is most relevant to human regeneration, the blood brain barrier is patent, and injury-induced cellular proliferation is normalizing.

A stimulation protocol of three one hour periods of phasic activity per day was based on previous findings that at least one hour of gait training per day was sufficient to double the number of progenitor derived neurons in the hippocampus of normal mice. Alternating stimulation of the common peroneal nerve stimulation produced alternating flexion of the hindlimbs that crudely approximated bilateral stepping-like movements of the hindlimbs.

The newborn cells mainly expressed markers of tripotential and glial progenitor cells, as well as astrocytes and oligodendrocytes. The number of BrdU labeled microglia, macrophages or endothelial cells was small and did not substantially contribute to the increased cell birth/survival at L1 and L5, levels distant from the injury site (T8/9). This conclusion is consistent with the very low contribution (fewer than 1.5%) of microglia and endothelial cells to total BrdU labeled cells in the normal spinal cord.

For unbiased quantitative analysis, advanced stereological methods were used that are well accepted in the field. The effect of FES was robust and selective and an effect of FES was not observed in normal uninjured rats. The validity of the stereological measures is supported by the fact that the total number of cells (labeling index: 2.61% of total nuclei) of newborn cells distant from the injury (e.g., C2) correlate closely with values obtained with similar BrdU labeling methods and stereological analysis in the normal rat spinal cord observed in other labs.

FES Increased Tripotential Progenitor Birth after SCI

A five-day interval of BrdU labeling will primarily label proliferating cells that do not have time to differentiate into mature cells, especially neurons. No evidence of new neuron birth was present in the spinal cord at day 0 or 7 after BrdU injection and this is consistent with previous data demonstrating the absence of new neuron birth in the adult spinal cord.

Figure 8:
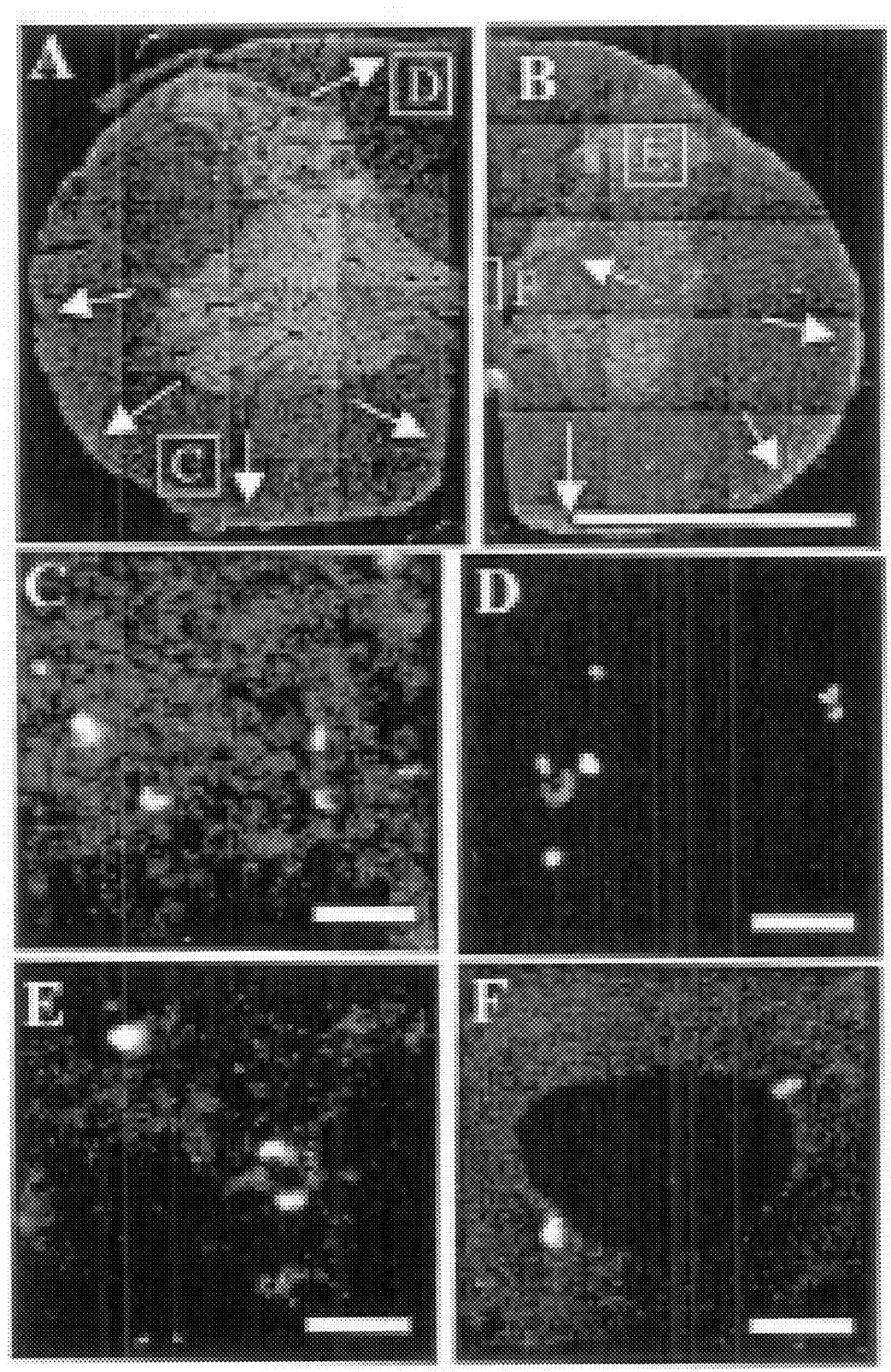
FIG. 8 shows new cell birth in the adult spinal cord after chronic SCI.

FIG. 8 shows new cell birth in the adult spinal cord after chronic SCI. Panels A & B show 40 μm coronal sections of the spinal cord at the C2 (A) and L1 (B) levels, which were immunolabeled with mouse anti-BrdU antibody. Sections were reconstructed using StereoInvestigator® from individual images at 20× magnification. Zones where the majority of BrdU positive cells were found are indicated with arrows. Square lettered inserts in panels A & B correspond to magnified images in panels C-F. Although the greatest number of BrdU positive cells was found in the white matter (C), BrdU positive cells were also present in grey matter (D-E) and around the central canal (F). Scale bar in panels A-B is 1 mm, and scale bar in panels C-F is 50 μm.

FIGS. 9(a) and (b) show that FES promoted new cell birth/ survival in the damaged spinal cord. Quantitative counts of BrdU labeled cells were performed using stereological methods in coronal spinal cord sections (C2-L5). Two-way ANOVA demonstrated the effects of treatment and spinal level (within groups, $p<0.05$). (A) FES induced a robust and selective increase in new cell birth reserved to lower lumbar segments that predictably experienced increased activity from the patterned FES induced stepping-like limb movements. (B) This effect persisted in the cell survival group 7 days later (*$p<0.05$; **$p<0.001$, FES vs. control).

Figure 10:
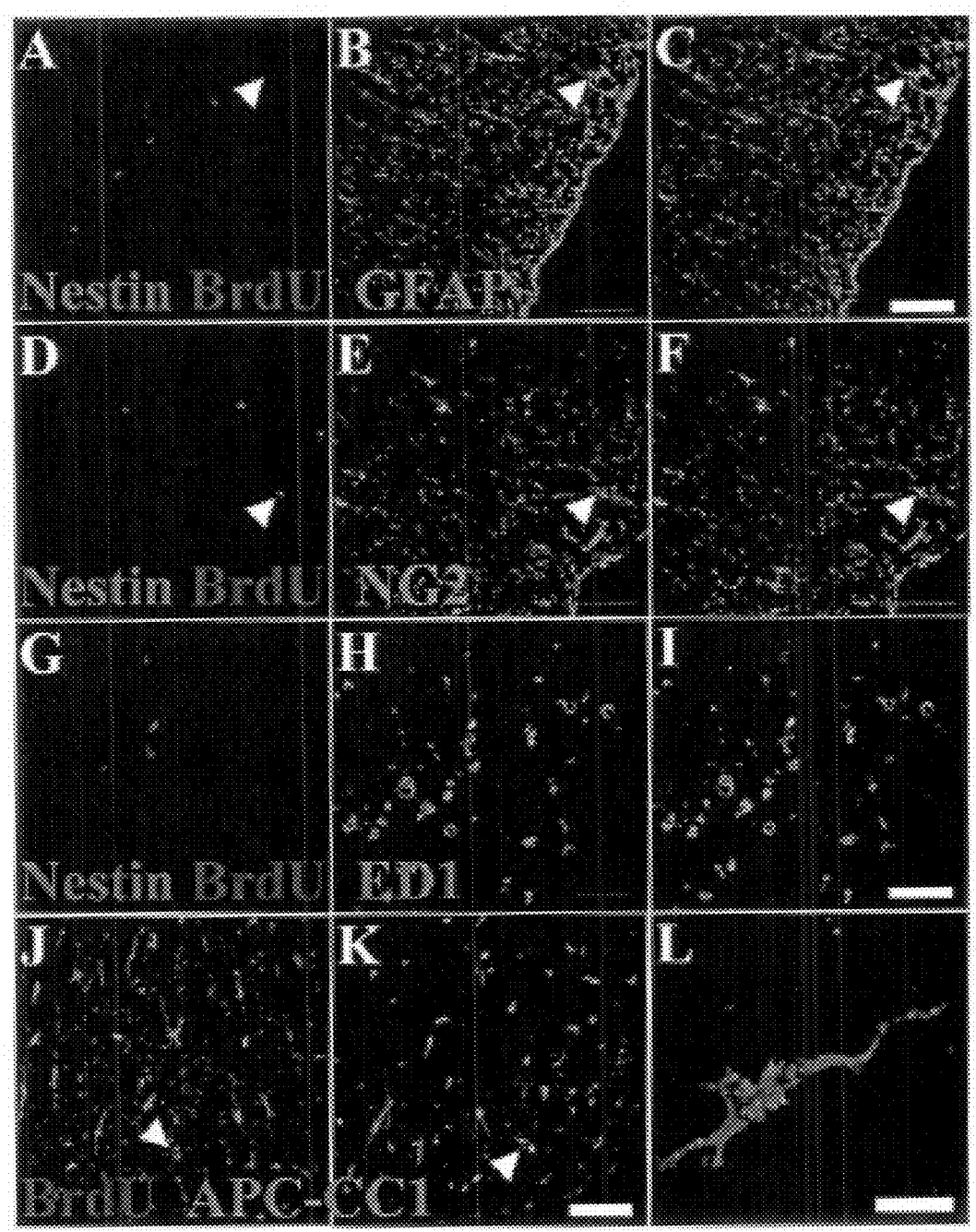
FIG. 10, (a)-(l) shows confocal microscopic images of anti-BrdU labelled and phenotype labelled cells identifying new-born cells as tripotential progenitor cells, glial progenitor cells, astrocytes and oligodendrocytes, from an FES-treated animal at lumbar level L5, two hours after the last BrdU injection.

FIG. 10, panels (a)-(l) shows BrdU colocalization with cell specific markers. Confocal microscopic images from an FES treated animal at lumbar level L5, two hours after the last BrdU injection. (A-C) Nestin immunoreactivity (blue) was found predominantly in white matter and labeled cells exhibited bipolar and multipolar morphology. Some of the Nestin+ cells colabeled with GFAP (green, arrowhead), which may represent reactive astrocytes, however, fewer than 2% double labeled with BrdU (red). Thus, BrdU+/Nestin+ cells are proliferating tripotential progenitors rather than reactive astrocytes. (D-F) Some BrdU+/Nestin+ cells double labeled with NG2 (green, arrowhead). These cells were usually located near the pial layer and showed bipolar morphologies. (G-I) Macrophages, here labeled with anti-ED1 (green), were located throughout the injured spinal cord. Fewer than 3% were BrdU+ and were only found at levels close to the injury site. No Nestin+/ED1+ cells were identified. (J-L) Throughout the spinal cord particularly in white matter (J=level C2, K=level L5) a small subset of BrdU+ cells that co-labeled with the oligodendrocyte marker APC-CC1 (green, arrowhead) was found. This ratio increased rapidly when observed 7 days after the last BrdU injection suggesting that many glial progenitors turn into oligodendrocytes. (L) Single confocal section of a BrdU+/APC-CC1+ cell. Scale bar (A-K)=50 μm, (L)=10 μm.

Figure 11:
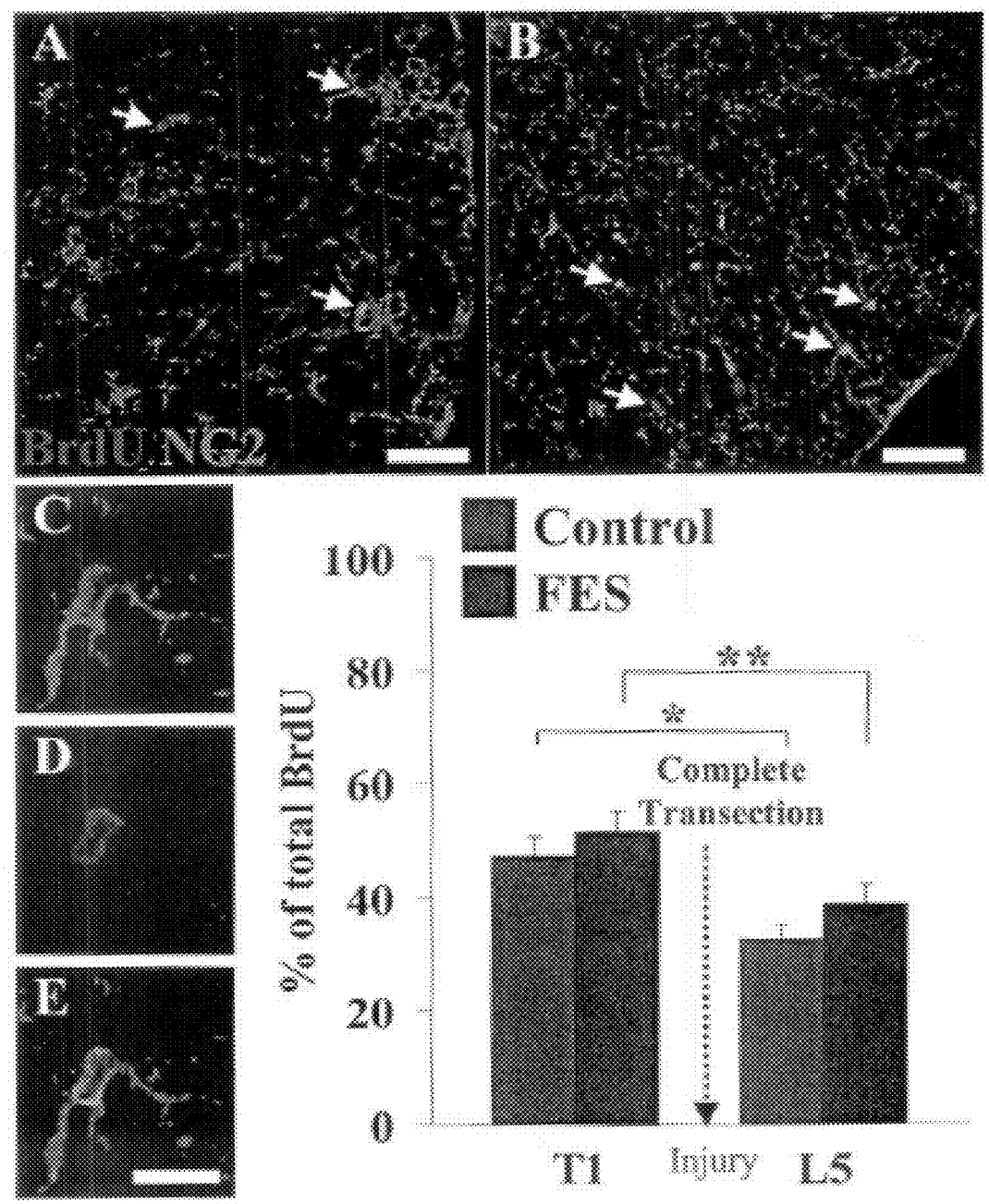
FIG. 11, (a)-(e) shows quantification of NG2 (glial progenitor cell marker) colocalization with BrdU following spinal cord injury at 2 hours after last BrdU injection.

FIG. 11, panels (a)-(e) shows quantification of NG2 colocalization with BrdU following SCI at 2 hours after last BrdU injection. NG2 immunoreactivity was used to classify BrdU+ cells as glial progenitor cells rostral (A) and caudal (B) to the lesion site. NG2+ cells displayed bipolar and multipolar cell morphologies predominantly in the white matter (arrows indicate individual BrdU+/NG2+ cells). Panels C-E depict single confocal sections of each marker for such an individual cell. The distribution pattern of Brdu+/NG2+ cells did not vary amongst groups. However there was a significant decrease of BrdU+/NG2+ immunoreactivity below the level of injury (47±3% at T1 and 51±3% at L5 in Control; 33±3% at T1 and 39±3% at L5 in FES treated animals) implying that there were fewer glial progenitors newly generated. Two-way ANOVA demonstrated the effect of spinal level (*$p<0.05$; **$p<0.001$, T1 vs. L5). Scale bar (A,B)=50 μm, (C-E)=10 μm.

Figure 12:
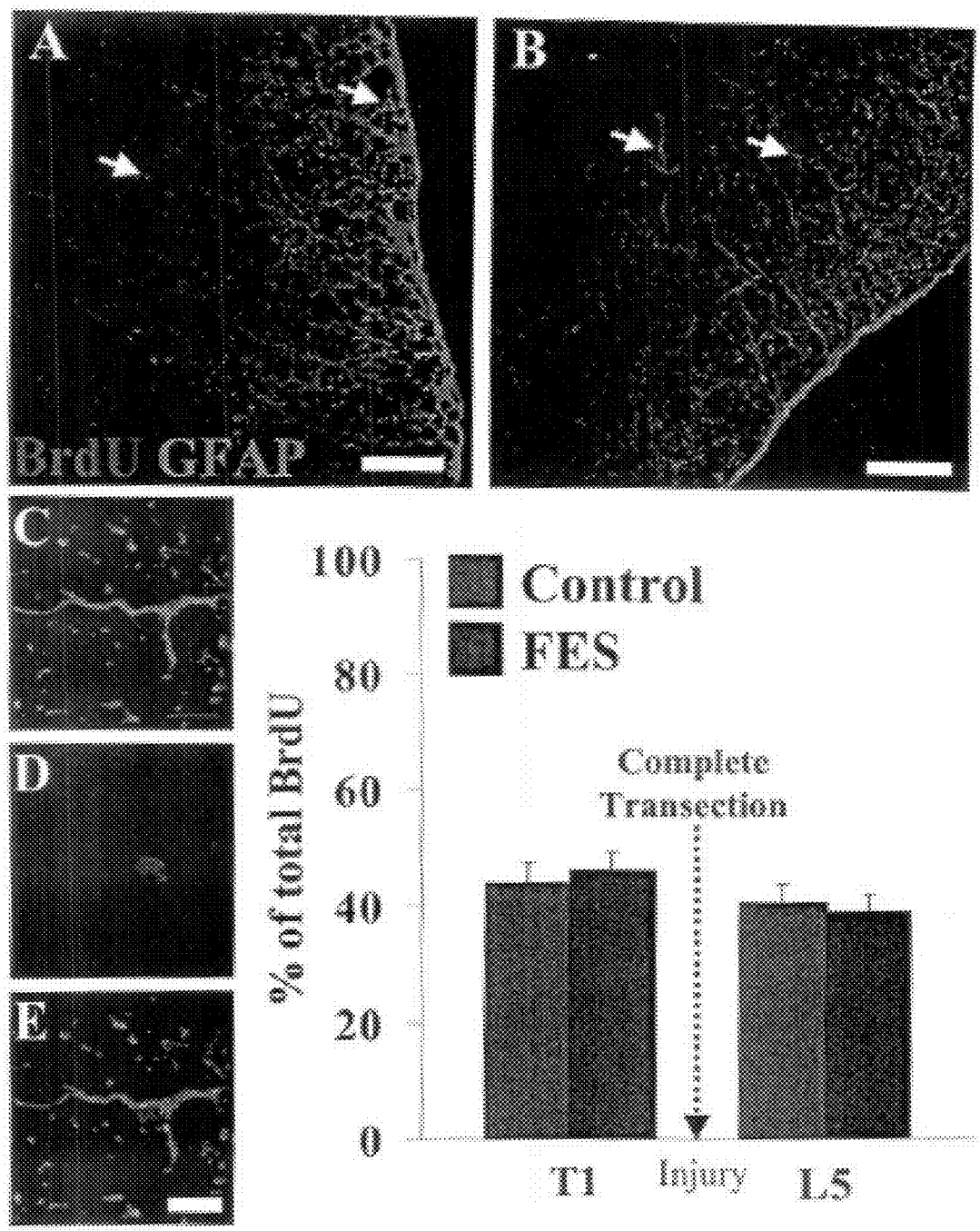
FIG. 12, (a)-(e) shows quantification of GFAP (astrocyte marker) colocalization with BrdU in the injured spinal cord at 2 hours after last BrdU injection.

FIG. 12, panels (a)-(e) shows quantification of GFAP colocalization with BrdU in the injured spinal cord at 2 hours after last BrdU injection. GFAP immunoreactivity was used to classify BrdU+ cells as astrocytes rostral (A) and caudal (B) to the lesion site. Labeled cells displayed predominantly multipolar cell morphologies (arrows indicate individual BrdU+/ GFAP+ cells). Panels C-E depict single confocal sections of each marker for an individual astrocyte. The distribution pattern of GFAP+ cells did not vary amongst groups. An effect of spinal level on the BrdU+/GFAP+expression was not identified. Scale bar (A,B)=50 μm, (C-E)=10 μm.

Figure 13:
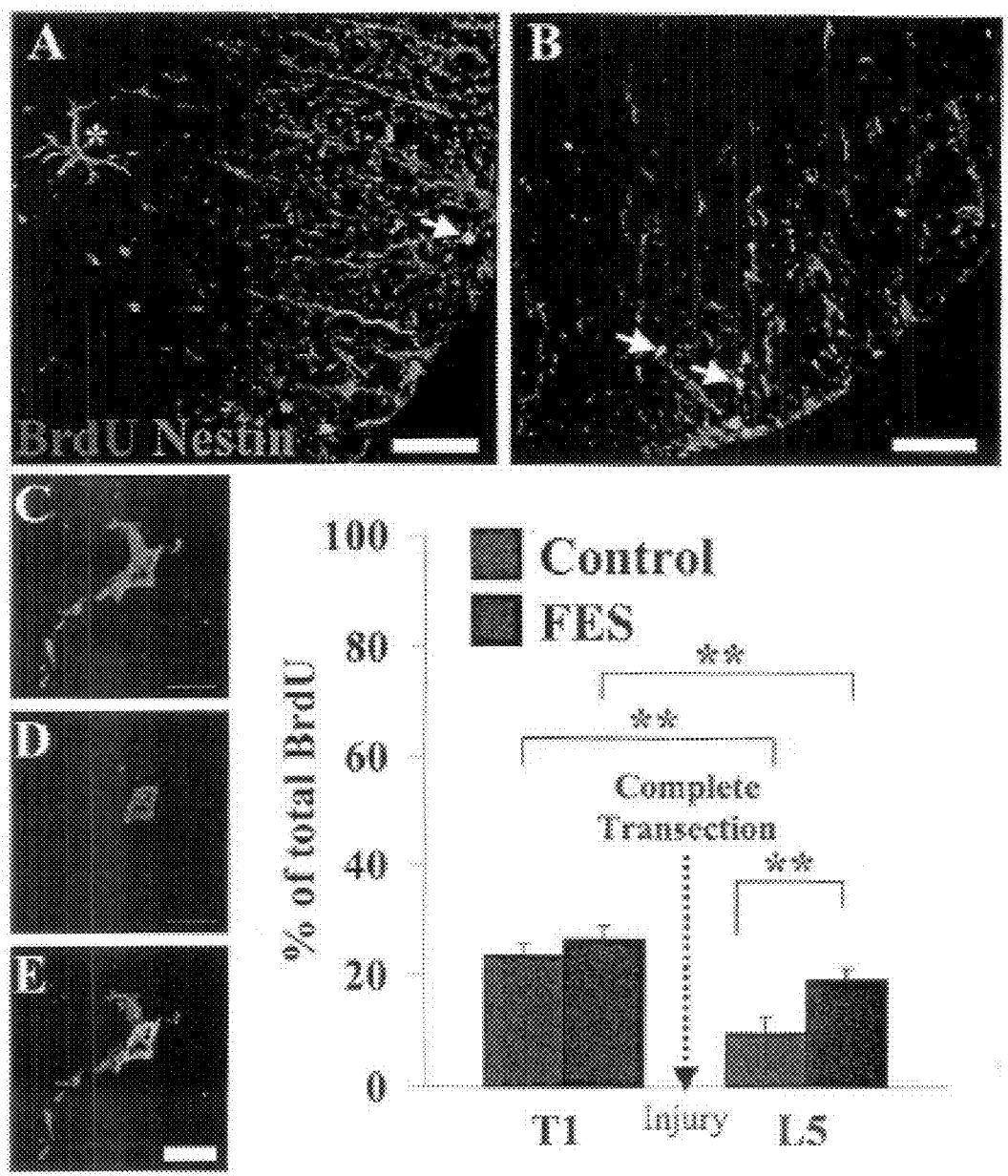
FIGS. 13, (a)-(e) shows quantification of Nestin (tripotential progenitor cell marker) colocalization with BrdU in the injured spinal cord at 2 hours after last BrdU injection.

FIG. 13, panels (a)-(e) shows quantification of Nestin colocalization with BrdU in the injured spinal cord at 2 hours after last BrdU injection. Nestin immunoreactivity was used to classify BrdU+ cells as tripotential progenitor cells found rostral (A) and caudal (B) to the lesion site (arrows indicate individual BrdU+/Nestin+ cells). Some of the Nestin+ cells show morphologic signs of reactive astrocytes (asterisk). However, fewer than 2% double labeled with BrdU. Panels C-E depict single confocal sections of a typical Nestin+/ BrdU+ cell. The distribution pattern of Nestin+ cells did not vary amongst groups rostral to the lesion site. However, as seen with NG2 (FIG. 4) there was an effect of spinal level (Two-way ANOVA, **$p<0.001$, T1 vs. L5). Most importantly, FES doubled the tripotential progenitor cell birth at L5. Scale bar (A,B)=50 μm, (C-E)=10 μm.

Quantitative analysis was conducted of progenitor phenotype at spinal levels T1 and L5 equidistant from the site of cord transection which enabled comparison of cell phenotypes in a region where FES had no effect and a region where the effects of FES were robust.

There were no quantitative differences in NG2+, GFAP+, or APC-CC1+ cell numbers, however, the number of Nestin+ cells doubled from 10±3% to 19±2% with FES treatment at level L5. Triple labeling procedures (BrdU/GFAP/Nestin) were used and confocal microscopy to rule out the possibility that the increase in Nestin expression was due to reactive astrocytosis caused by SCI or FES. However, the ability to identify the phenotypes of the majority of cells contributing to the enhanced cell birth was limited as in previous studies.

Cell Survival was Decreased Below the Level of Injury

The effect of FES to increase the numbers of BrdU-labeled progenitors persisted for at least one week following labeling. However, FES did not alter the percentage of surviving BrdU labeled cells. Seven days after BrdU labeling, cell survival in both groups was significantly decreased at all levels below the injury site (T11, L1, L5). In contrast, cell survival above the level of injury (C2, T7) was largely unchanged. After SCI, neural activity is dramatically reduced in regions below the injury level. The present invention demonstrates, however, that FES appears to preferentially affect cell birth rather than survival. It is likely that activity may be required for optimal differentiation and survival of progenitors, and the limited survival effect of FES treatment may reflect a quantitative limit of activity induced by the present FES paradigm.

Implications of FES-Induced Neural Progenitor Proliferation on Regeneration and Recovery after SCI The present invention represents the first demonstration that FES can enhance cellular generation in the injured adult CNS. Although electrical stimulation is used clinically to attempt to enhance bone fusion and stimulate peripheral nerve growth, it has not been applied to CNS regeneration. The magnitude of the cell birth/survival response to FES in the present study was surprisingly large (61% to 77%). Based on the volume of the entire adult rat spinal cord (estimated by volume displacement; 506±7 mm$^3$, density=1.21 g/cm$^3$) and the estimates of FES induced cell birth, at level C2 approximately two new cells are born per second in the current studies. Therefore, a million new cells were born in just under one week, a number equivalent to numbers commonly transplanted in the injured spinal cord for repair purposes. Harnessing the potential of these endogenously born cells therefore represents a rational approach to self-repair of the damaged CNS. Experiments found in the Examples section of the present invention were designed to optimize the experimental analysis of one index of regeneration and new cell birth.

The data suggests that FES may enhance recovery after chronic spinal cord injury. FES dramatically increases cell birth/survival in the injured spinal cord may be one factor that could contribute to functional recovery. Activity-based recovery applications may be an important long-term therapeutic target for individuals with SCI.

The effect of stepping-like limbs movements, produced by alternating bilateral FES of the common peroneal nerve on cell genesis at six levels (C2, T1, T7, T11, L1, and L5) proximal and distal to complete spinal transection, was examined. FIG. 11 illustrates the experimental outline and the topographic relationship between the injury level and the FES stimulation level.

FES Reduced the Incidence of Medical Complications

The incidence of bladder infections was reduced in groups that received FES (incidence of 85±8% in control versus 65±10% in FES treated animals over 12 days; p<0.05, Students t-test, n=12 per group). Bladder infections were defined by onset of bloody or cloudy urine coinciding with presence of red and white blood cells, struvite crystals, and epithelial cells in the urine sediment. Neither group showed any signs of autophagia, pain, or inflammation.

The Majority of Newly Born Cells were Located in White Matter

Anti-BrdU labeled cells indicative of new cell birth occurred in the spinal cords of both control and stimulated rats. Although it is possible that BrdU may integrate into apoptotic cells as a result of DNA damage repair, BrdU does not integrate in detectable levels into adult cells induced to undergo necrotic or apoptotic death. These data are in accordance with observations in this study that BrdU positive cells do not colabel with anti activated Caspase-3 antibody, a marker of cells dying by apoptosis (data not shown). Thus, the BrdU positive nuclei evaluated in this study represent dividing cells.

The majority of labeled cells were found in the white matter rather than the gray matter, in keeping with previous reports of new cell birth in the uninjured adult rats spinal cord. Anti-BrdU labeled cells were present in gray matter, particularly the dorsal horns, and a small number of labeled cells were present around the central canal. The data may reflect migration and do not directly assess the location of the cell birth.

FES Produced a Selective and Robust Enhancement of New Cell Birth/Survival

Quantitative stereological analysis indicated that both spinal level and presence of electrical stimulation were significant factors in determining the numbers of BrdU labeled cells. A dramatic and statistically significant increase in cell birth was observed in the FES group selective to the lumbar cord, the area expected to have enhanced activity as a result of the FES-induced hindlimb movements (FIG. 8). Cell birth in the FES group increased by 61±18% at L1 and 77±11% at L5 (labeling index, control vs. FES, n=6 per group: L1: 2.58 vs. 4.16, p=0.02, L5: 1.86 vs. 3.29, p<0.001). Comparable numbers of new cells between groups were present at T11 (4.17 vs. 3.83 cells/mm$^3$, p=0.48) and above the transection (T1, T7 and C2). Importantly, the effect of FES persisted when cell survival was examined 7 days after the last BrdU injection (labeling index, control vs. FES, n=6 per group: L1: 1.62 vs. 2.29, p<0.001, L5: 1.58 vs. 2.39, p<0.001).

FES Had No Effect in the Healthy Spinal Cord

To set the baseline of cell birth in Long Evans rats and to evaluate the interactive effects of injury and FES we compared the results to a group (n=6) of non-injured rats that received the exact FES treatment and BrdU injection paradigm. The animals were sacrificed 2 hours after the last BrdU injection. There was no difference in number of BrdU positive cells between groups at any level (labeling index, control vs. FES, n=3 per group: C2: 1.15 vs. 1.17, T1: 1.2 vs. 1.0, T7: 1.18 vs. 1.05, T11: 1.12 vs. 1.32, L1: 1.17 vs. 0.9, L5: 0.83 vs. 0.8). There were significantly fewer cells born in the normal cord than in the injured spinal cord (labeling index, SCI control vs. NO injury control: C2: 2.3 vs. 1.2; T1: 3.0 vs. 1.2; T7: 4.1 vs. 1.2; T11: 4.2 vs. 1.1; L1: 2.6 vs. 1.2; L5: 1.9 vs. 0.8).

Most BrdU Labeled Cells were Found Surrounding the Lesion Site

Figure 9:
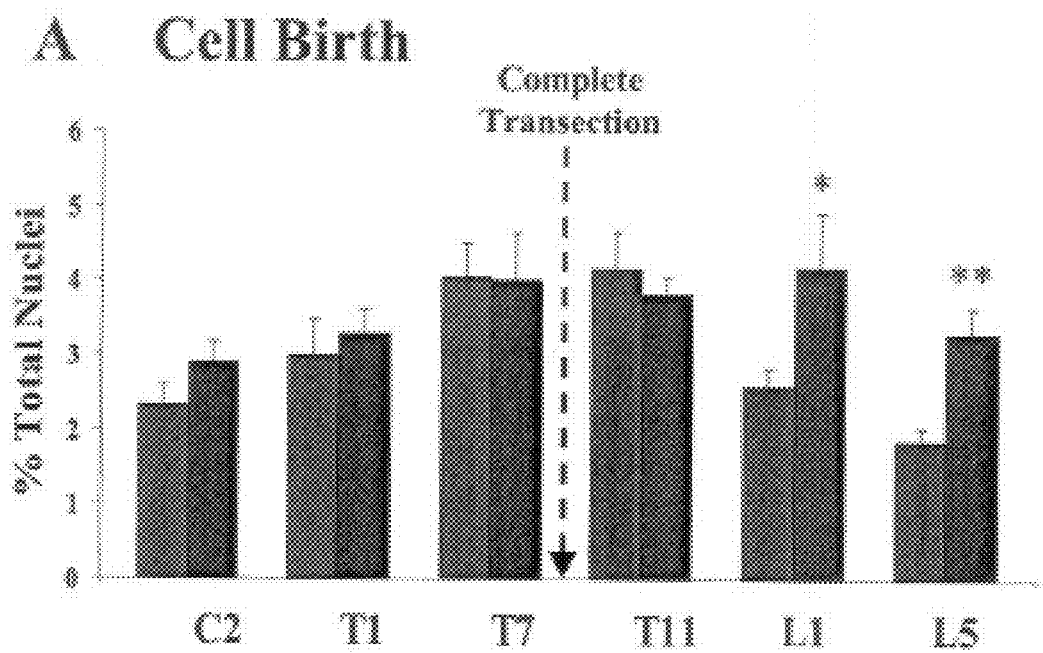
FIG. 9(a) shows results of quantitative counts of BrdU labeled cells showing FES-induced selective increase in new cell birth reserved to lower lumbar segments.
FIG. 9(b) shows that the effect demonstrated in FIG. 8(a) persisted in the cell survival group 7 days later.
Figure 9:
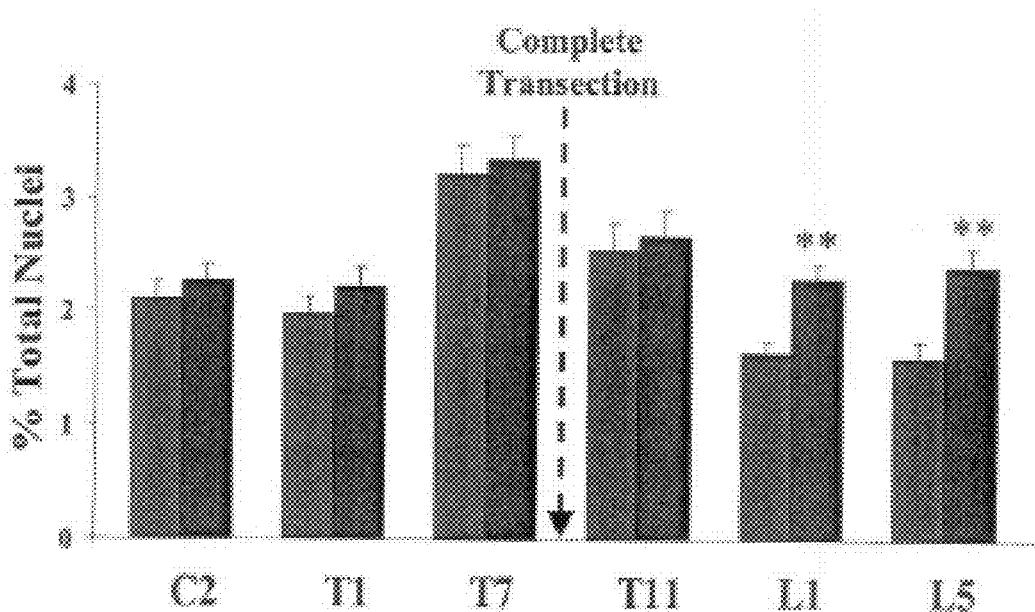

The injury associated pattern of cell birth/survival above the lesion were similar between the two groups and were consistent with previous work demonstrating that SCI induces new cell birth (FIG. 13). There was a significant increase in cell birth/survival surrounding the spinal cord lesion compared to distant C2 and L5 levels (C2 vs. T7: 65±13%; C2 vs. T11: 58±9%; L5 vs. T7: 113±9%; L5 vs. T11: 107±12%; Two way ANOVA: all comparisons shown above were significant p<0.05, n=6 in the control group). In the FES treated group similar differences were observed in cell numbers above the lesion but not below (FIG. 9).

BrdU Labeled Cells Expressed Mainly Glial and Progenitor Markers

Figure 14:
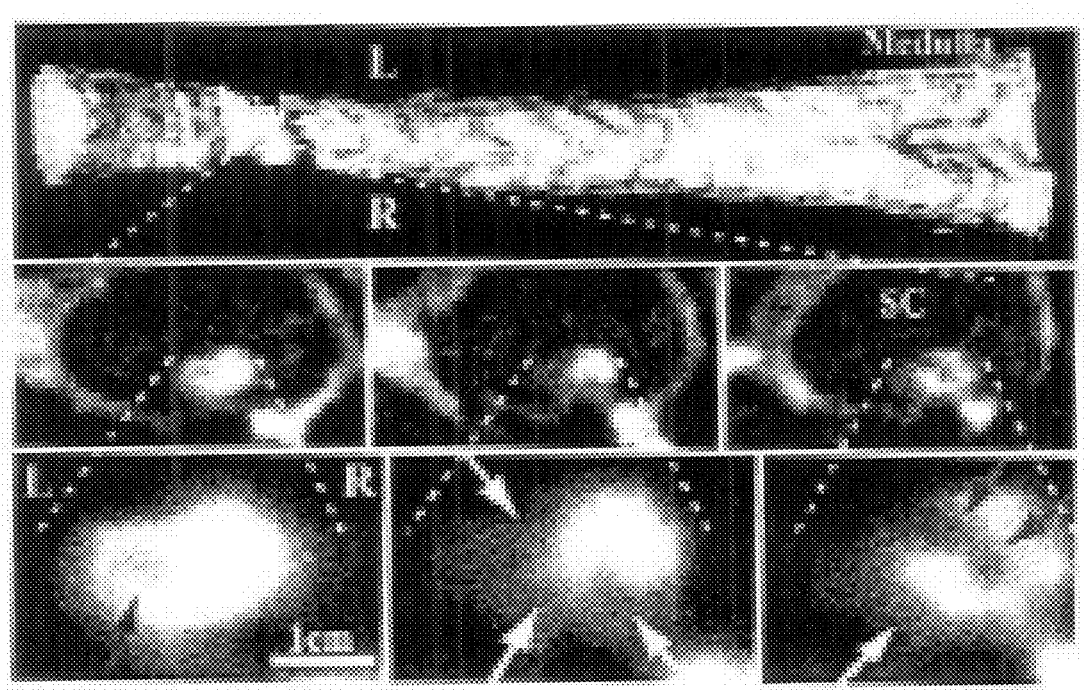
FIG. 14 show multiple views of a T1-weighted MRI of cervical SCI in the SCI subject of FIGS. 1-6.
Figure 15:
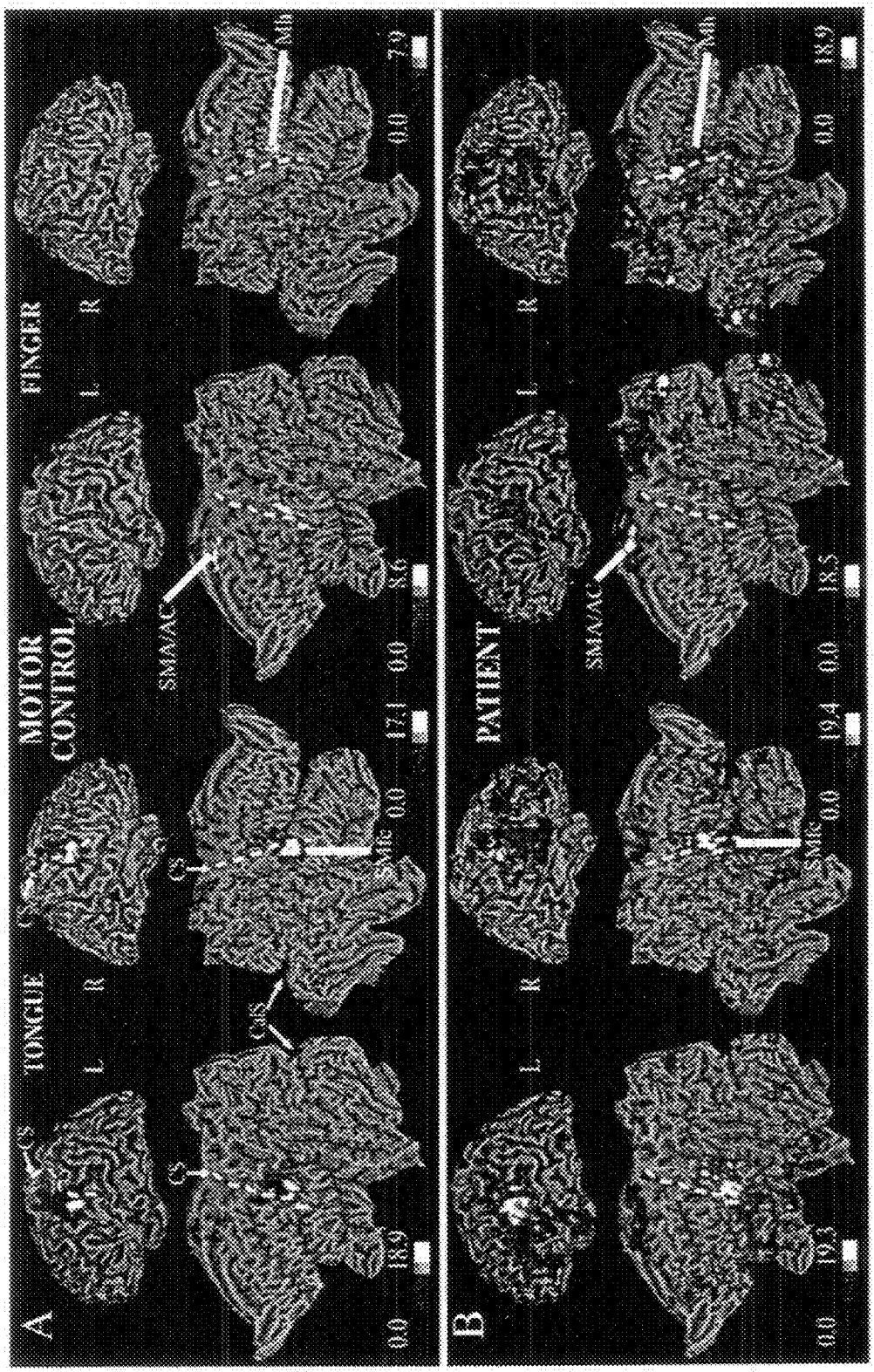
FIG. 15 shows 3D and 2D flattened views of an atlas brain with projected BOLD responses for visuomotor tracking task.
Figure 16:
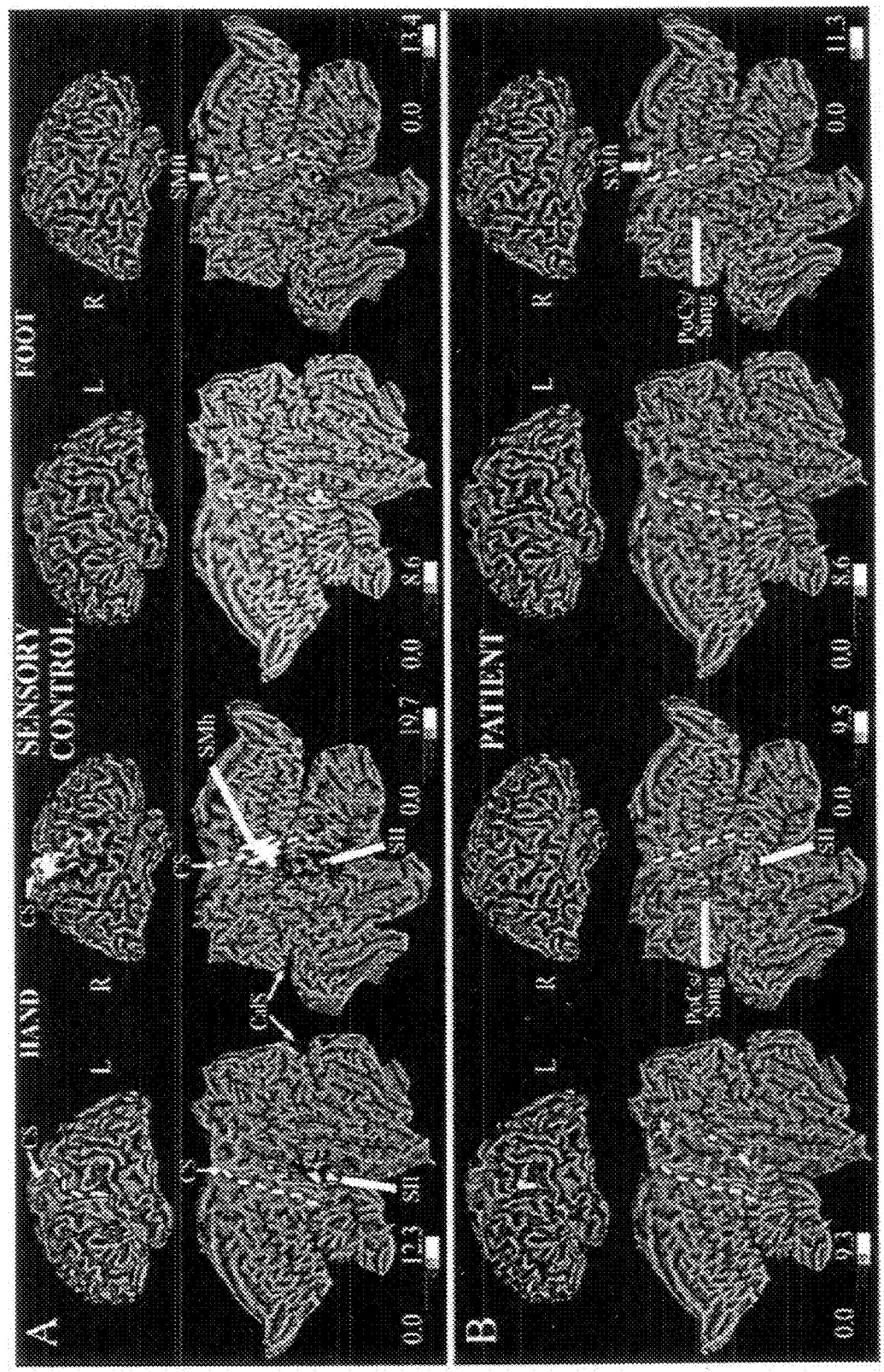
FIG. 16 shows 3D and 2D flattened views of the atlas brain in which BOLD responses for sensory vibrotactile stimuli have been projected.

Phenotypic analysis of anti-BrdU labeled cells in both groups indicated that the majority of cells born and evaluated immediately following the 5 day BrdU pulse labeling were neural cells, especially in segments distant to injury (C2, T1, L1, and L5). Anti-BrdU labeled cells expressed markers of tripotential progenitors (Nestin), glial progenitors (NG2), astrocytes (GFAP) and oligodendrocytes (APC-CC1). There was no quantitative difference in NG2 (49±3% at T1; 36±3% at L5), GFAP (45±3% at T1; 40±3% at L5), or APC-CC1 (fewer than 5%) expression between groups (FIG. 14-16). However, the number of Nestin positive cells nearly doubled with FES treatment from 10±3% to 19±2%, level L5. To distinguish between BrdU/Nestin positive tripotential progenitors and proliferating postmitotic astrocytes, triple labeling procedures were performed with GFAP. The majority (>90%) of BrdU/Nestin positive cells did not express GFAP. Therefore, most of the phenotypically identifiable cells are tripotential progenitors (FIG. 10). The limited ability to identify the majority of increased numbers of cells is in keeping with similar low percentages in previous studies.

Microglia, Macrophages, and Endothelial Cells Minimally Contributed to Increased Cell Birth/Survival Surrounding the Lesion Site To examine the possibility that other non-neural cell types contributed to the total cell birth/survival measured in this study, the presence of tissue macrophages were determined, and microglia using the marker anti-ED1 and OX-42 (FIG. 10). ED-1 and OX-42 labeled macrophages and microglia surrounding the injury site and their numbers rapidly tapered as a function of distance from the injury site. Macrophages could also be easily distinguished by their characteristic cell body shape and eccentric nuclei and their bifringent inclusions. Double labeling with anti-BrdU revealed that a very small number of these cells were BrdU positive (fewer than 2%). Anti-BrdU labeling was also occasionally observed in endothelial cells or pericytes of blood vessels (identified by characteristic morphology, location and immunoreactivity to specific markers (anti-CD31, anti-Glut-1)), but the total number of cells was small (fewer than 1.5%) and mostly restricted to the levels surrounding the injury site (T8/T11). Thus, microglia, macrophages, and endothelial cells did not contribute substantially to the number of BrdU labeled cells measured at levels distant from the injury (C2, T1, L1, and L5).

Absence of Neurogenesis after Spinal Cord Injury

Despite a careful search for cells double-labeled with anti-BrdU and early or late neuronal markers (anti-NeuN, anti-TUJ1, anti-PSA-NCAM, and anti-doublecortin) newborn neuronal phenotypes were not identified. It is believed that the spinal cord was examined at too early a point in the recovery to see direct evidence of neurons, and that later studies examining later stages in recovery will reveal the presence of neurons consistent with increased birth and survival of neural cells and with recovery of function.

Example 3

Functional Reorganization and Stability of the CNS in the Human Subject

The functional organization of somatosensory and motor cortex was investigated in an individual with a high cervical spinal cord injury, the human subject of Example 1, supra. As described above, the subject demonstrated a 5-year absence of nearly all sensory and motor function at and below the shoulders, and a rare and surprising recovery of some function in years 6-8 after intense and sustained rehabilitation therapies. The results are described fully in Corbetta et al, Proc. Natl. Acad. Sci. 99: 17066-71 (Dec. 24, 2002), which is herein incorporated by reference in its entirety, together with the primary references contained therein.

Functional magnetic resonance imaging (fMRI) was used to study the subject's brain activity in response to vibratory stimulation and voluntary movements of body parts above and below the lesion. No response to vibratory stimulation of the hand was observed in the primary somatosensory cortex (SI) hand area, which was conversely recruited during tongue movements that normally evoke responses only in the more lateral face area. This result suggests SI reorganization analogous to previously reported neuroplasticity changes after peripheral lesions in animals and humans. In striking contradistinction, vibratory stimulation of the foot evoked topographically appropriate responses in SI and second somatosensory cortex (SII). Motor cortex responses, tied to a visuomotor tracking task, displayed a near typical topography, although they were more widespread in premotor regions. These findings are consistent with preservation of motor and some somatosensory cortical representations in the absence of overt movements or conscious sensations for several years after spinal cord injury and have implications for future rehabilitation and neural-repair therapies.

Severe sensory deprivation due to amputation or peripheral nerve damage profoundly alters responsiveness and topographical organization of primary somatosensory cortex (SI). Less well known are the alterations in cortical responses after spinal cord injury (SCI). Individuals with SCI, as opposed to those with amputations, retain a normal body, which may influence cortical reorganization significantly, especially in individuals with partial SCI who have surviving fibers and potentially some functional connections across the level of damage. It will become an important practical issue to assess cortical responsiveness immediately after damage and in the course of recovery if ongoing efforts for restoring function by transplantation or other means such as FES-evoked patterned movement, are successful. Functional MRI (fMRI) with blood oxygenation level-dependent (BOLD) contrast provides a noninvasive method to assess neuronal activity by monitoring task-related changes in the local tissue concentration of deoxyhemoglobin.

These fMRI results provide mapping of cortical somatosensory-motor areas in the human subject. Given the unique medical history of the subject in including late partial recovery of function after being clinically assessed as motor complete and nearly sensory complete, the fMRI study sought to determine the topographical normality of the subject's somatosensory and motor cortical responses above and below the level of damage, and to investigate possible cortical reorganization subsequent to a late recovery from SCI.

Subjects. Example 1 describes in detail the clinical history of the 50-year-old right-handed male who sustained a displaced C2 type II odontoid fracture from an equestrian accident in 1995 at age 42. No other permanent injuries, particularly a head injury, complicated the SCI. By clinical assessment, motor or somatosensory functions were absent below the lesion level for 5 years except for spotty sensation in the left hemitorso. He is ventilator dependent with hypophonic vocalization due to impaired function of the chest diaphragm and muscles of vocalization. The control subject was a 23-year-old male who has a normal neurological and psychiatric history.

Visuomotor Tracking. Subjects were required to synchronize movements to a video image of a yellow-green tennis ball against a black background. Subjects viewed the image on a back projection screen, which was seen in a mirror mounted on the head coil. The ball ($\approx 4°$ in diameter) jumped regularly left/right of a fixation point ($\approx 4°$ jumps, 0.83-Hz rate) to guide tongue left/right movements (tongue extruded and moved against lips), jumped above/below the fixation point to guide left index-finger movement (at metacarpal-phalangeal joint) and remained stationary for rest periods. Visual monitoring indicated that both subjects consistently followed the ball motion. Movement range and vigor were less in the SCI subject. The left index finger was tested because the SCI subject sustained better following with this finger movement. Subjects could not see their finger during fMRI. For testing consistency all tactile stimulation was also applied to the left extremities.

Vibrotactile Stimulation. A massage vibrator delivered suprathreshold tactile stimulation. The device, previously used in positron-emission tomography studies, was made magnetic resonance-compatible by replacing the electric motor with a pneumatic drive that was connected to a remote air compressor. The vibrator delivered approximately 2-mm displacement vibrations centered on a base frequency of approximately 100 Hz. The vibrator head was manually held against the left fingers and palm or sole of the left foot throughout stimulation and rest periods. Precise skin displacements were unknown, although stimulus magnitudes probably activated most skin mechanoreceptors, adjoining deeper tissues, and proprioceptors throughout distal parts of the stimulated limb.

MRI Acquisitions. During MRI the SCI subject was ventilated, and physiologic parameters were monitored continuously (Magnitude/Millenium anesthesia monitoring, In Vivo Research, Orlando, Fla.) in a custom magnetic resonance-compatible setup (Shielding Resources Group, Tulsa, Okla.). All MRI used a 1.5-Tesla Magnetom Vision scanner and circularly polarized head coil (Siemens, Erlangen, Germany). Structural 3D T1-weighted magnetization-prepared_rapid gradient echo MRI was acquired. fMRI used a custom T2*-weighted asymmetric spin-echo echo-planar sequence sensitive to BOLD contrast (repetition time=2,360 ms, T2* evolution time=50 ms, $\alpha=90°$). During each fMRI run, 128 sets of 20 contiguous, 6-mm thick slices were acquired parallel to the anterior commissure posterior commissure plane (3.75×3.75 mm in-plane voxel size), allowing complete brain coverage. This protocol yielded images of the SCI subject without significant signal loss or distortions in the brain despite surgical metal in the neck. Sensory and motor fMRI were acquired in different imaging sessions by using 8-10 fMRI runs per session and 128 frames (346.75 s) per run. For sensory fMRI, four runs were obtained for each stimulated limb, and each run contained eight baseline frames followed by 15 trials with three frames of stimulation alternating with five frames of no stimulation. For motor fMRI, four to five runs were obtained for each task (tongue and finger), each run having 12 trials of five task frames alternating with five rest frames.

MRI Data Analysis. The cord was segmented from structural MRI for area measurement and 3D-rendered display by using ANALYZE AVW 4.0 (Mayo Foundation, Rochester, Minn.) and a Sun Fire V880 computer (Sun Microsystems, Santa Clara, Calif.). fMRI data were analyzed as described in Burton et al., J. Neurophysiol. 87: 589-607 (2002), and Corbetta et al., Neuron 21: 761-73 (1998). General linear models estimated the BOLD responses in each subject and each task (e.g., tongue movement) without assuming a hemodynamic response shape. BOLD time courses were estimated in each voxel, over eight frames (21.67 s) for somatosensory tasks and 10 frames (27.09 s) for motor tasks. fMRI data were smoothed with a 3D 2-voxel Gaussian kernel and transformed to the Talairach atlas before statistical analysis. Statistical maps were based on cross-correlation between estimated BOLD time course and a reference hemodynamic response function that was obtained by convolving a delayed gamma function with a rectangular function representing task and control periods. The derived t statistics per voxel were converted to normally distributed z scores and corrected for multiple comparisons across the entire brain by using distributions obtained from Monte Carlo simulations (based on methods described in S. D. Forman et al., Magn. Reson. Med. 33:636-47 (1995). These images were inspected by using a threshold of $P=0.05$ for a z score value of 4.5 over at least three face-contiguous voxels. The statistical maps were projected onto a standard brain atlas in both 3D view of the lateral hemispheric surface and 2D view of flattened cortex (Van Essen et al., Proc. Natl. Acad. Sci. USA 95: 788-95 (1998); see http://stp.wustl.edu/resources/caretnew.html).

Structural MRI of the Cord. T1-weighted MRI in the SCI subject showed greater than 75% loss in cross-sectional tissue area throughout the C2 region.

FIG. 14 shows a T1-weighted MRI of cervical SCI in SCI subject. The top panel shows longitudinal 3D-rendered image (view from behind) of lower-brainstem and cervical spinal cord segments from the tip of the C2 odontoid process through the bottom of the C2 vertebral body. The middle panel shows selected low-magnification images through the zone of injury show the small size of the cord relative to the spinal canal (SC). Images are transverse to the cord's long axis and at levels 40, 46, and 51 mm below the cerebellar tonsils (Left, Center, and Right, respectively). The bottom panel shows higher-magnification view of the same three transverse images show focal regions of low T1-weighted signal that are consistent with chronic tissue damage (myelomalacia) or scarring. The location and shape of these sites vary and include a central oval (red arrow), a cleft (blue arrow), and several peripheral lesions (yellow arrows). L indicates left, R, indicates right.

Additionally, there were multiple focal areas of tissue damage (myelomalacia) in different parts of the remaining spinal cord. The continuity of white-matter pathways across the lesion cannot be determined from these images alone, particularly given the small cord size and the multiple areas of damage within and across levels.

Clinical History of SCI Patient. Initial recovery of motor and somatosensory function began in year 2000 after several years of standard physical therapy including passive range of motion and supported standing. The recovery accelerated through 2002 after the subject was enrolled in a more intense regime of physical therapy. Physical therapy included thrice-weekly, hour-long sessions of functional electrical stimulation of leg muscles that was computer synchronized to drive an exercise bicycle as sown in FIG. 2. Frequent standard clinical examinations in the last 2 years documented self-initiated small movements with the left index finger, right wrist, and more recently, lower extremities. In parallel, the SCI subject reported feeling strong sensation upon tactile stimulation and passive movement of the upper and lower extremities. Sensations from the lower extremities were stronger. He had good accuracy in roughly localizing a tactile stimulus on the hand or foot including dorsal and volar surfaces. He also could identify a stimulated finger or toe (fingers better than toes).

Motor Tracking Tasks. FIG. 15 shows BOLD responses to the visually guided motor tasks on 3D and flattened representations of a standard brain. 3D and 2D flattened views of an atlas brain are shown with projected BOLD responses for visuomotor tracking task; the color scale indicates z scores. FIG. 15A shows a control subject, while FIG. 15B shows the subject with SCI.

Tongue movements in the control subject activated a ventral segment of precentral gyrus, central sulcus, and postcentral gyrus bilaterally (FIG. 15A, SMfc). These regions likely correspond to the primary sensory and motor cortex face area. Recruitment of SI in a visuomotor tracking task probably reflects tactile and proprioceptive sensory feedback signals associated with normal movements. Significant activity also occurred in medial frontal cortex along the cingulate sulcus (supplementary motor area/anterior cingulate) and in visual occipital cortex.

Left index-finger movements produced the strongest activation in a middle segment of the contralateral (right) precentral gyrus_sulcus (FIG. 15A, Mh). This response was approximately 2 cm superior to the foci active during tongue movements. Smaller responses occurred in the right parietal operculum and bilaterally within the central sulcus and postcentral gyrus (SI, area 3b); these likely related to sensory feedback.

Finally, bilateral responses were observed in supplementary motor area/anterior cingulate similar to those observed for tongue movements. In the subject with SCI, BOLD responses during both motor tasks were stronger and more widespread than those observed in the control subject (FIG. 15 B vs. A). Tongue movements activated the face area of SI/M1 in ventral precentral gyrus, central sulcus, and postcentral gyrus (primary somatosensory-motor cortex, SMfc). Activity spread dorsally into the hand area and more extensively into adjacent regions such as the second somatosensory cortex (SII) and frontal operculum.

There was also strong activation of dorsolateral prefrontal cortex and supplementary motor area/anterior cingulate. Left index-finger movements intensely activated the contralateral M1 hand area (Mh), frontal operculum, SII, cingulate cortex, and lateral and medial parietal cortex (FIG. 15B). There was no spread into the SI/M1 face area. Recruitment of visual cortex, both ventrally and dorsally, was much stronger in the SCI than control subject and during finger than tongue movements in the SCI subject (FIG. 15B). In one experiment, fMRI was acquired while the SCI subject performed left finger movements without visual feedback for 20-s intervals. Voluntary movements were internally planned and executed after a brief verbal "GO" signal. Performance was less accurate and less sustained, and the subject reported more effort, compared with visuomotor tracking. BOLD responses (movement vs. rest) were weaker and less localized in M1, and there was no recruitment of premotor or higher-order regions (not shown).

Vibrotactile fMRI. FIG. 16 shows BOLD responses to vibratory stimulation of the left hand or left foot. 3D and 2D flattened views of the atlas brain are shown, on which BOLD responses for sensory vibrotactile stimuli have been projected; the color scale indicates z scores. FIG. 16A shows results for a control subject, and FIG. 16B shows those for the Subject with SCI.

In the control subject (FIG. 16A), left hand and fingers vibration activated the contralateral (right) SI/M1 cortex. Responses occupied the dorsal segment of the postcentral gyrus extending into the central sulcus and the precentral gyrus, thus identifying the normal location of the hand area (FIG. 16A, SMh). There was also bilateral activation of SII. Left foot vibration evoked activity in the right medial frontal gyrus approximately 1.2 cm dorsal to the hand area (FIG. 16A Right). This response likely involved the SI/M1 foot area (SMft). SII was activated bilaterally. The subject with SCI reported a better sensation of vibration in the left foot than in the left hand. Left hand vibration failed to activate expected hand areas of SI/M1 in the right postcentral gyrus, central sulcus, and precentral gyrus but produced bilateral responses in SII (FIG. 16B, Left).

Several other regions not recruited in the control subject responded in the SCI subject. These regions included, in order of strength, the contralateral (right) postcentral sulcus, and bilaterally, the posterior postcentral gyrus, and supramarginal gyrus (PoCs/5 mg); the ipsilateral (left) postcentral gyrus; and contralateral medial frontal gyrus near the SI/M1 foot area. The contralateral regions correspond to likely higher-order somatosensory areas. Left foot stimulation in the SCI subject (FIG. 16B Right) elicited a normal contralateral response in the right medial frontal gyrus, central sulcus, and postcentral gyrus that corresponds to the normal SI/M1 foot area (SMft, compare FIG. 16 A with B). An ipsilateral SI response also occurred in the left hemisphere. SII responses again were located along the parietal operculum but were weaker than during hand stimulation.

There was some recruitment of higher-order parietal regions in right supramarginal gyrus during foot stimulation. The fMRI from the SCI was overlaid with those of control subjects to compare somatosensory-motor cortex areas. FIG. 17A contrasts activation maps for left hand vibration and tracking tongue movements in the control subject. FIG. 17B shows the absence of a normal hand area in the SCI subject. FIG. 17C shows that the face area is similarly active in both subjects. However, the active region expands dorsally in the SCI subject where it encroaches onto the normal hand area (FIG. 17D).

Functional MRI in the SCI subject with late partial recovery of sensorimotor function revealed BOLD responses in the SI foot area during vibratory foot stimulation, responses in higher-order somatosensory areas during stimulation of the hand, and responses in motor cortex areas during finger movements. In contrast, no response was observed in the S1 hand area upon vibratory hand stimulation. This region instead was recruited during sensory-motor stimulation of the tongue and lips. The brain responses to vibratory stimuli occurred despite greater than 75% loss in spinal cord area and multiple regions of chronic damage in the remaining cord. These responses indicate the existence of functional neural connections that traverse the site of cord injury. The subject's late clinical recovery is surprising given the 5-year history of no voluntary movements and nearly absent sensations from the extremities. Some brain responses were consistent with known neuroplasticity effects demonstrated mostly in animal studies, while others were entirely unexpected and are consistent with preservation of normal topography and recruitment of compensatory areas.

The S1 hand area responded to sensory stimulation of the face but not the hand, which possibly reflects neural plasticity based on competitive interaction from a normally innervated face. This response of the (deafferented) hand area to (invading) face inputs might correlate with an enhanced resolution of tactile sensation in the face, as demonstrated on a much smaller spatial scale within the digit representation of monkey area 3b.

The reorganization possibly involved subcortical transneuronal changes, which are progressive and delayed. Cortical activity is likely to reflect this mechanism by initial silence followed by late recovery of responses. Similar to prior results in monkeys with long-term dorsal rhizotomies, expansion in the SCI subject involved SI hand area responses to stimulation in the lower face, which borders the thalamic hand area. A conjunction of mechanisms is likely to be responsible for the SI foot-area responses and the reported better sensations from the foot. Absent was competition from intact representations because all cortical and subcortical areas adjacent to the foot were severely deprived. This likely left the SI foot area accessible to any input that was conveyed through surviving fibers at the level of the injury (FIG. 14).

Clinical changes accelerated after more intense rehabilitation involving FES-evoked patterned movement of the lower extremities in accordance with the methods of the present invention. The SCI subject was able to localize tactile stimulation on the hand, despite little evidence of responses in the SI hand area to intense tactile vibrations. Vibratory stimulation of the hand recruited SII and additional postcentral and posterior parietal somatosensory regions that normally do not respond during passive stimulation but become active during attention-requiring tactile discrimination tasks. In addition, recruitment of more posterior multimodal parietal regions was observed.

In contrast to the changes found in somatosensory maps, the primary motor areas were more nearly normal despite years without movements. Finger movement activated a confined middle segment of M1, whereas tongue movements, although activating hand SI areas, did not invade adjacent M1 regions.

The secondary motor areas (premotor and cingulate cortex) were activated more in the SCI vs. control subject. Additionally, many higher-order regions (e.g., posterior parietal, temporal, and dorsolateral prefrontal cortex) were recruited in the SCI subject, more for finger than tongue movements. Although tongue movements use neurons above the lesion, it is not surprising that an abnormally widespread network of activity was evoked, because these movements require coordination of several muscle groups (e.g., diaphragm or accessory respiratory muscles) that have C2-C5 myotomes at or below the lesion.

Coupling of visual and motor information aided motor performance and led to stronger, more widespread activity compared with self-timed movements. The differences in visually guided vs. nonguided movements cannot be explained solely by a greater effort or lack of proprioceptive feedback, because these effects were similar in the two tasks. Thus, it is likely that the regular oscillation of the tennis ball image provided necessary timing and directional information to plan and execute more sustained and regular movements.

In studies of SCI without recovery, normal motor cortical responses have been found during attempted/imagined toe movements in 9/9 subjects with thoraco-lumbar paraplegia but weaker sensory cortical responses to passive unconscious mobilization in 3/9 subjects. Normal SII activation has been described in 3/3 paraplegics but only weak SI foot activation in one subject. The data herein extend those studies by assessing preservation and rearrangement of cortical topography (face vs. hand vs. foot) in the rare case of partial recovery years after SCI.

The finding of any normal topography in somatosensory and motor areas of a tetraplegic is surprising given a long history of no sensations or movements from below the injury. These fMRI findings were coincident with the extraordinary and intensive rehabilitation therapies including a program of FES-evoked patterned movement in a patient with severe but not total SCI.

The mere presence of these cortical responses years after deafferentation is consistent with the goal of therapeutic strategies aimed at restoring spinal cord connections because they suggest that restoration of neural links across the lesion appear capable of reestablishing motor and sensory functions.

Other Embodiments

The detailed description set-forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description which do not depart from the spirit or scope of the present inventive discovery. Such modifications are also intended to fall within the scope of the appended claims.

REFERENCES CITED

All publications, patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

What is claimed is:

1. A method for treating central nervous system (CNS) damage in a mammalian subject in need of such treatment comprising:
    inducing a therapeutically effective amount of functional electrical stimulation (FES)-evoked patterned movement in a mammalian subject for a period of time sufficient to regenerate neural cells; and
    monitoring the mammalian subject for CNS neural regeneration or CNS motor function;
    wherein
        the patterned movement occurs during exposure to FES; and
        at least a portion of lost motor function or sensory function of the mammalian subject lost is restored; and
        the CNS damage comprises (i) an acute trauma or (ii) a chronic disease.

2. The method of claim 1 wherein the acute trauma is selected from the group consisting of complete severance of the spinal cord, partial severance of the spinal cord, and stroke.

3. The method of claim 1 wherein the chronic disease selected from the group consisting of multiple sclerosis, cancer, tumor metastasis, Huntington's Disease, Alzheimer's disease, amyotrophic lateral sclerosis, and neurodegenerative effects of aging.

4. The method of claim 1 wherein the therapeutically effective amount of FES-evoked patterned movement promotes neural cell birth.

5. The method of claim 1 wherein the therapeutically effective amount of FES-evoked patterned movement enhances neural cell survival.

6. The method of claim 1 wherein the therapeutically effective amount of FES-evoked patterned movement enhances neural signal transmission capacity.

7. The method of claim 6 wherein the therapeutically effective amount of FES-evoked patterned movement initiates synaptic changes in neural cells such that the neural cells reconfigure with neural cells to form new synaptic connections in or around a site of CNS damage.

8. The method of claim 1 wherein the mammalian subject is motor complete or sensory complete.

9. The method of claim 1 wherein the neural cells comprise at least one of tripotential progenitor cells, glial progenitor cells, astrocytes and oligodendrocytes or any combination thereof.

10. The method of claim 1 wherein the FES-evoked patterned movement activates a central pattern generator in the spinal cord.

11. The method of claim 1 wherein the patterned movement comprises at least one of walking, breathing, biking, punching, kicking, swimming, fist clinching, toe pointing, knee bending, hip flexing, sitting, standing, and jumping.

12. The method of claim 11, wherein the FES is applied to at least one muscle or muscle group selected from the group consisting of gluteals, paraspinal, abdominals, wrist extensors, wrist flexors, deltoids, biceps, triceps, hamstrings, and quadriceps.

13. The method of claim 1, wherein the application of functional electrical stimulation is applied to a muscle or muscle group externally.

14. The method of claim 1, wherein the application of functional electrical stimulation is applied to a muscle or muscle group internally.

15. The method of claim 1, wherein the FES-evoked patterned movement occurs for at least about one hour per day and at least three times per week.

16. The method of claim 1 wherein said therapeutically effective amount of FES-evoked patterned movement comprises delivering electronic stimulation at 3 V and 200 µs monophasic pulses delivered at 20 Hz.

17. The method of claim 1, wherein the neural cells are capable of transmitting an at least partially restored neural signal.

18. The method of claim 17, wherein the at least partially restored neural signal begins in the brain of the subject and ends in a muscle in communication with a peripheral nervous system nerve cell.

19. The method of claim 18, wherein the at least partially restored neural signal ending in a peripheral nervous system nerve cell causes the muscle to contract.

20. The method of claim 19, wherein inducing a therapeutically effective amount of FES-evoked patterned movement comprises stimulation of peripheral nervous system sufficient to evoke a cycle of neural signal activity in the peripheral nerves and in the spinal cord, followed by neural signal inactivity therein, and wherein the cycle is repeated.

21. The method of claim 20, wherein the neural signal cycle is sufficient to evoke the muscles to perform patterned movement.

22. The method of claim 21, wherein said patterned movement comprises reciprocal movements.

23. The method of claim 1, comprising monitoring the mammalian subject for CNS neural regeneration.

24. The method of claim 23, wherein monitoring the mammalian subject for CNS neural regeneration comprises fMRI imaging.

25. The method of claim 1, comprising monitoring the mammalian subject for CNS motor function.

26. The method of claim 1, wherein the patterned movement comprises biking and the FES is applied to at least a gluteal muscle, a quadricep muscle, and a hamstring muscle.

27. The method of claim 26 wherein the FES-evoked patterned movement occurs for at least about one hour per day and at least three times per week.

* * * * *